US012421483B2

(12) United States Patent
Smith

(10) Patent No.: US 12,421,483 B2
(45) Date of Patent: Sep. 23, 2025

(54) BIOFABRICATION SYSTEM

(71) Applicant: THE TRUSTEES OF INDIANA UNIVERSITY, Indianapolis, IN (US)

(72) Inventor: Lester J. Smith, Maud, TX (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 967 days.

(21) Appl. No.: 17/599,838

(22) PCT Filed: Apr. 3, 2020

(86) PCT No.: PCT/US2020/026632
§ 371 (c)(1),
(2) Date: Sep. 29, 2021

(87) PCT Pub. No.: WO2020/210126
PCT Pub. Date: Oct. 15, 2020

(65) Prior Publication Data
US 2022/0135922 A1    May 5, 2022

Related U.S. Application Data

(60) Provisional application No. 62/831,366, filed on Apr. 9, 2019.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/12* (2013.01); *C12M 23/34* (2013.01); *C12M 23/38* (2013.01);
(Continued)

(58) Field of Classification Search
CPC ....... C12M 21/08; C12M 23/12; C12M 23/34
See application file for complete search history.

(56) References Cited

U.S. PATENT DOCUMENTS

2002/0106625 A1    8/2002  Hung et al.
2002/0115585 A1    8/2002  Hei
(Continued)

FOREIGN PATENT DOCUMENTS

CA        3049944 A1 *  7/2018   ......... C12M 1/3407
EP        2151491 A2    2/2010
WO     2018035182 A1    2/2018

OTHER PUBLICATIONS

Mohammad Amin Shamekhi, et al., "Fabrication and characterization of hydrothermal cross-linked chitosan porous scaffolds for cartilage tissue engineering applications," Mater Sci Eng C Mater Biol Appl. 80:532-542. doi: 10.1016/j.msec.2017.03.194. Epub Mar. 27, 2017. (Year: 2017).*

(Continued)

*Primary Examiner* — Elizabeth A Robinson
*Assistant Examiner* — Jonathan E Lepage
(74) *Attorney, Agent, or Firm* — Barnes & Thornburg LLP

(57) ABSTRACT

A system with reusable components and methods are disclosed for culturing, forming, perfusing, and maintaining a perfusible-tissue construct. The system uses a production container comprising a floor, a wall extending from the floor, wherein the floor and wall define a production reservoir, a formation section defined in the floor, wherein the formation section comprises at least one well, and a grip extending outwardly from the formation section; wherein the production container is made of a biocompatible material that remains stable when autoclaved.

15 Claims, 19 Drawing Sheets

(51) Int. Cl.
*C12M 1/12* (2006.01)
*C12M 1/32* (2006.01)
*C12N 5/00* (2006.01)

(52) U.S. Cl.
CPC ............ *C12M 23/48* (2013.01); *C12M 25/02* (2013.01); *C12M 29/10* (2013.01); *C12M 29/20* (2013.01); *C12M 47/02* (2013.01); *C12N 5/0068* (2013.01)

(56) References Cited

U.S. PATENT DOCUMENTS

2010/0273253 A1    10/2010  Teixeira de Oliveira et al.
2013/0029875 A1*  1/2013  Stehno-Bittel ......... C12M 23/12
                                                        435/395

OTHER PUBLICATIONS

PCT International Search Report and Written Opinion completed by the ISA/US on Feb. 4, 2021 and issued in connection with PCT/US2020/026632.

* cited by examiner

BIOFABRICATION SYSTEM

CROSS-REFERENCE TO RELATED APPLICATIONS

This application is a U.S. national counterpart application of international application serial No. PCT/US2020/026632 filed Apr. 3, 2020, which claims priority to U.S. Provisional Patent Application No. 62/831,366, filed Apr. 9, 2019, the disclosures of which are hereby expressly incorporated by reference in their entireties.

STATEMENT OF GOVERNMENT SUPPORT

This invention was made with government support under OD023595 and TR002529 awarded by National Institutes of Health. The government has certain rights in the invention.

TECHNICAL FIELD

The present disclosure relates to scientific tools, and more particularly to a system for forming, culturing, and analyzing a perfusible tissue.

BACKGROUND

Current tissue biofabrication techniques are complex, delicate, difficult to implement, and rely on expensive robotic bioprinters. The Regenova Bio 3D Printer, for example, costs $450,000, weighs several hundred pounds, uses expensive consumables (many of which are discarded after one use), and has a foot print of two average-sized refrigerators. A need exists for low-cost tissue biofabrication techniques, devices, and scientific tools that are reusable, and fit easily on a lab bench.

SUMMARY

According to an aspect of the disclosure, a production container comprises a floor, a wall extending from the floor, wherein the floor and wall define a production reservoir, a formation section defined in the floor, wherein the formation section comprises at least one well, and a grip extending outwardly from the formation section; wherein the production container is made of a biocompatible material that remains stable when autoclaved.

In some embodiments, a capture container comprises a capture foundation having a top surface and a bottom surface, wherein the top surface defines a conically shaped capture reservoir having a vertex, and the bottom surface defines a capture channel; and wherein the capture container is made of a biocompatible material that remains stable when autoclaved.

In some embodiments, a micro-tissue production component, comprises a production container, comprising: a floor, a wall extending from the floor, wherein the floor and wall define a production reservoir, and wherein the wall includes a top edge, a formation section defined in the floor, wherein the formation section comprises at least one well, a grip extending outwardly from the formation section; and a capture container, comprising: a capture foundation having a top surface and a bottom surface, wherein the top surface defines a conically shaped capture reservoir, and the bottom surface defines a capture channel, wherein the production container's top edge is positioned to contact the capture container's top surface, and wherein the micro-tissue production component is made of a biocompatible material that remains stable when autoclaved.

In some embodiments, a platen, comprises a top surface having a conically shaped platen reservoir, wherein the platen reservoir comprises a vertex having a porous section comprising a flat surface and at least one opening; and a bottom surface defining a platen channel; wherein the platen is made of a biocompatible material that remains stable when autoclaved.

In some embodiments, an undercast comprises a floor having at least one relief port; a wall extending outwardly from the floor; a perfusible-formation section defined by a grip insert surrounding a platform, and at least one member, wherein the at least one member extends outwardly from the platform, wherein the perfusible-formation section is coupled to the floor, and an undercast channel defined by the floor, the wall, and the grip insert, wherein the undercast channel extends between the wall and the perfusible-formation section.

In some embodiments, a small undercast, comprises a base; an intermediate section; and at least one member, wherein the intermediate section couples the base to the at least one member, and wherein the at least one member extends outwardly from the intermediate section.

In some embodiments, a perfusible-tissue formation component, comprises an undercast comprising: a floor having at least one relief port; a wall extending outwardly from the floor; an undercast channel defined by the wall; a perfusible-formation section defined by a grip insert surrounding a platform, and at least one member, wherein the at least one member extends outwardly from the platform, wherein the perfusible-formation section is coupled to the floor, and wherein the undercast channel extends between the wall and the perfusible-formation section; and a platen comprising: a top surface having a conically shaped platen reservoir, wherein the platen reservoir comprises a vertex having a flat surface and at least one opening, and a bottom surface defining a platen channel; wherein the platen channel is positioned to receive the grip insert of the undercast, and the at least one member traverses the at least one opening; and wherein the perfusible-tissue formation component is made of a biocompatible material that remains stable when autoclaved.

In some embodiments, a perfusible-tissue formation component, comprises an undercast, comprising: a base; an intermediate section; and at least one member, wherein the intermediate section is configured to couple the base to the at least one member, and wherein the at least one member extends outwardly from the intermediate section; and a platen comprising a top surface having a conically shaped platen reservoir, wherein the platen reservoir comprises a vertex having a flat surface and at least one opening, and a bottom surface defining a platen channel; wherein the at least one opening is positioned to receive the at least one member, and wherein the perfusible tissue-formation component is made of a biocompatible material that remains stable when autoclaved.

In some embodiments, a bioreactor, comprises a base having at least one well defined therein; wherein the at least one well has a floor and a wall, at least one inlet port in fluid communication with the at least one well, at least one outlet port in fluid communication with the at least one well, a raised grip coupled to and extending outwardly from the floor of the well; and wherein the bioreactor is made of a biocompatible material that remains stable when autoclaved.

In some embodiments, a micro-tissue capture component comprises a bioreactor, comprising: a base having at least one well defined therein; wherein the at least one well has a floor and a wall, at least one inlet port in fluid communication with the at least one well, at least one outlet port in fluid communication with the at least one well, a raised grip coupled to and extending outwardly from the floor of the well; and a capture container, comprising: a capture foundation having a top surface and a bottom surface, wherein the top surface defines a conically shaped capture reservoir, and the bottom surface defines a capture channel; wherein the capture channel is positioned to receive the raised grip; wherein the well is configured to receive the capture container, and wherein the micro-tissue capture component is made of a biocompatible material that remains stable when autoclaved.

In some embodiments, a perfusible-tissue formation component comprise a bioreactor, comprising: a base having at least one well defined therein; wherein the at least one well has a floor and a wall, at least one inlet port in fluid communication with the at least one well, at least one outlet port in fluid communication with the at least one well, a raised grip coupled to and extending outwardly from the floor of the well; and a platen, comprising: a top surface having a conically shaped platen reservoir, wherein the platen reservoir comprises a vertex having a porous section comprising a flat surface and at least one opening, and a bottom surface defining a platen channel; wherein the platen channel is positioned to receive the raised grip of the bioreactor, wherein the well is configured to receive the platen, and wherein the perfusible-tissue formation system is made of a biocompatible material that remains stable when autoclaved.

In some embodiments, a kit comprises a micro-tissue production component having a production container, comprising: a floor, a wall extending from the floor, wherein the floor and wall define a production reservoir, and wherein the wall includes a top edge, a formation section defined in the floor, wherein the formation section comprises at least one well, a grip extending outwardly from the formation section, and a capture container, comprising: a capture foundation having a top surface and a bottom surface, wherein the top surface defines a conically shaped capture reservoir, and the bottom surface defines a capture channel, wherein the production container's top edge is positioned to contact the capture container's top surface, and wherein the micro-tissue production component is made of a biocompatible material that remains stable when autoclaved, and a perfusible-tissue formation component comprising: an undercast comprising: a floor having at least one relief port; a wall extending outwardly from the floor; a perfusible-formation section defined by a grip insert surrounding a platform, and at least one member, wherein the at least one member extends outwardly from the platform, wherein the perfusible-formation section is coupled to the floor, and an undercast channel defined by the floor, the wall, and the grip insert, wherein the undercast channel extends between the wall and the perfusible-formation section; and a platen, comprising: a top surface having a conically shaped platen reservoir, wherein the platen reservoir comprises a vertex having a porous section comprising a flat surface and at least one opening, and a bottom surface defining a platen channel; wherein the platen channel is positioned to receive the grip insert of the undercast, and the at least one member traverses the at least one opening; and wherein the perfusible-tissue formation component is made of a biocompatible material that remains stable when autoclaved, and a bioreactor, comprising: a base having at least one well defined therein; wherein the at least one well has a floor and a wall, at least one inlet port in fluid communication with the at least one well, at least one outlet port in fluid communication with the at least one well, a raised grip coupled to and extending outwardly from the floor of the well; and wherein the bioreactor is made of a biocompatible material that remains stable when autoclaved.

In some embodiments, a method of forming a perfusible-tissue construct, comprises (i) culturing cells in a production container to form at least one micro-tissue, the production container comprising: a floor, a wall extending from the floor, wherein the floor and wall define a production reservoir, a formation section defined in the floor, wherein the formation section comprises at least one well, and a grip extending outwardly from the formation section; wherein the production container is made of a biocompatible material that remains stable when autoclaved; (ii) removing the at least one micro-tissue from the production container and placing it in a capture container, the container comprising: a capture foundation having a top surface and a bottom surface, wherein the top surface defines a conically shaped capture reservoir, and the bottom surface defines a capture channel, and wherein the capture container is made of a biocompatible material that remains stable when autoclaved; (iii) centrifuging the capture container, (iv) removing the centrifuged at least one micro-tissue from the capture container and placing it onto a perfusible-tissue formation component comprising an undercast, comprising: a base; an intermediate section; and at least one member, wherein the intermediate section couples the base to the at least one member, and wherein the at least one member extends outwardly from the intermediate section; and a platen comprising (a) a top surface having a conically shaped platen reservoir, wherein the platen reservoir comprises a vertex having a flat surface and at least one opening, and (b) a bottom surface defining a platen channel; wherein the at least one opening is positioned receive the at least one member, and wherein the perfusible tissue-formation component is made of a biocompatible material that remains stable when autoclaved; and (v) removing the undercast from the platen to reveal a perfusible-tissue construct.

In some embodiments, the method further comprises, placing the platen comprising perfusible-tissue construct into a bioreactor comprising: (a) a base having at least one well defined therein; wherein the at least one well has a floor and a wall, (b) at least one inlet port in fluid communication with the at least one well, (c) at least one outlet port in fluid communication with the at least one well, (d) a raised grip coupled to and extending outwardly from the floor of the well; and wherein the bioreactor is made of a biocompatible material that remains stable when autoclaved, wherein the platen channel is positioned to receive the raised grip of the bioreactor, wherein the well is configured to receive the platen.

In some embodiments, the method further comprises perfusing the perfusible-tissue construct by flowing a media through the bioreactor using tubing and a pump configured to control the flow of media.

BRIEF DESCRIPTION OF THE DRAWINGS

The detailed description particularly refers to the following figures, in which.

DETAILED DESCRIPTION

Figure 1:
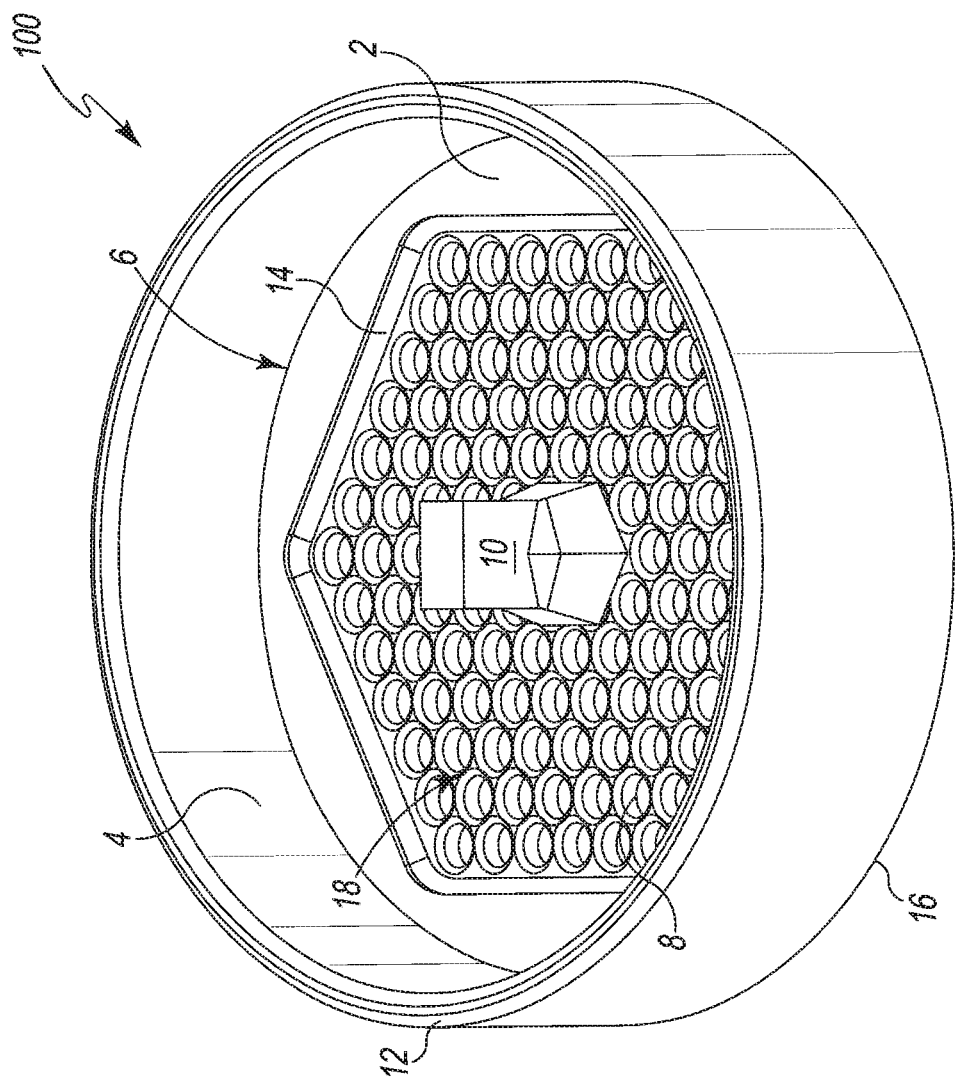
FIG. 1 is a perspective view of a production container.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

As used herein the term "autoclave" means a combination of heat and pressure wherein the temperature can be at least about 90° C., at least about 95° C., at least about 100° C., at least about 105° C., at least about 110° C., at least about 115° C., at least about 120° C., at least about 125° C., or at least about 130° C. The pressure can be at least about 0 psi, at least about 0.5 psi, at least about 1 psi, at least about 1.5 psi, at least about 2 psi, at least about 2.5 psi, or at least about 3 psi. In some embodiments, the pressure can be at least about 5 psi, at least about 7 psi, at least about 9 psi, at least about 11 psi, at least about 13 psi, at least about 15 psi, or at least about 17 psi.

As used herein the term "stable" means that a component remains functional for its intended purpose.

A biofabrication system is herein described comprising a micro-tissue production component, a perfusible tissue formation component 600, and a bioreactor 700. The biofabrication system is configured to be reusable and lab-bench scale. These two characteristics offer advantages over competitor products because the biofabrication system is cost-effective, reduces waste, and creates a smaller foot-print in a lab than other systems. The biofabrication system is made of materials that remain stable when autoclaved. Additionally, the materials may be cleaned without causing damage. In some embodiments, the biofabrication system may be cleaned using chemical reagents. Examples of such reagents include 70% ethanol, hydrogen peroxide, phosphate-buffered solution (PBS) and platinum discs. In some embodiments, parts of the biofabrication system is made of a material that is optically clear.

The micro-tissue production component comprises a production container 100 and a capture container 200 configured to couple together. The micro-tissue production component comprising the production container 100 and capture container 200 remain stable when autoclaved. The micro-tissue production component is configured to culture and form cell-dense micro-tissues and to capture those cell micro-tissues. The production container 100 and the capture container 200 are configured to be manipulated aseptically using a tool. An example of a tool is a pair of forceps.

In some embodiments, the production container 100 comprises a floor 2, a wall 4 extending from the floor 2, wherein the floor 2 and wall 4 define a production reservoir 6. In one embodiment, a formation section 18 is defined in the floor 2, and the formation section 18 comprises at least one well 8, and a grip 10 extending outwardly from the formation section 18. The wall 4 includes a top edge 12 and a bottom edge 16. The production container 100 further comprises a bottom surface 22.

Referring to FIG. 1, is an example of a production container 100 comprising a floor 2, a wall 4 extending from the floor 2, wherein the floor 2 and the wall 4 define a production reservoir 6. The wall 4 further having a top edge 12 and a bottom edge 16. A formation section 18 is defined in the floor 2, and the formation section 18 comprises a boundary wall 14 surrounding a plurality of wells 8 and a grip 10 extending outwardly from the formation section 18.

In some embodiments, the production reservoir 6 is configured to hold up to about 1 milliliter of fluid. In some embodiments, the production reservoir 6 is configured to hold up to 5 milliliters of fluid.

In some embodiments, the boundary wall 14 is configured to control and hold the over flow of media from the plurality of wells 8. In some embodiments, the production reservoir 6 of the production container 100 is configured to contain media used to grow and culture the cell-dense microtissues. In some embodiments, the production container 100 does not include a boundary wall 14.

In some embodiments, the floor 2 is substantially flat so that it is parallel to a surface that the production container 100 is resting on. In some embodiments, the floor 2 is concave, wherein the floor 2 slopes down towards the formation section 18.

Figure 2:
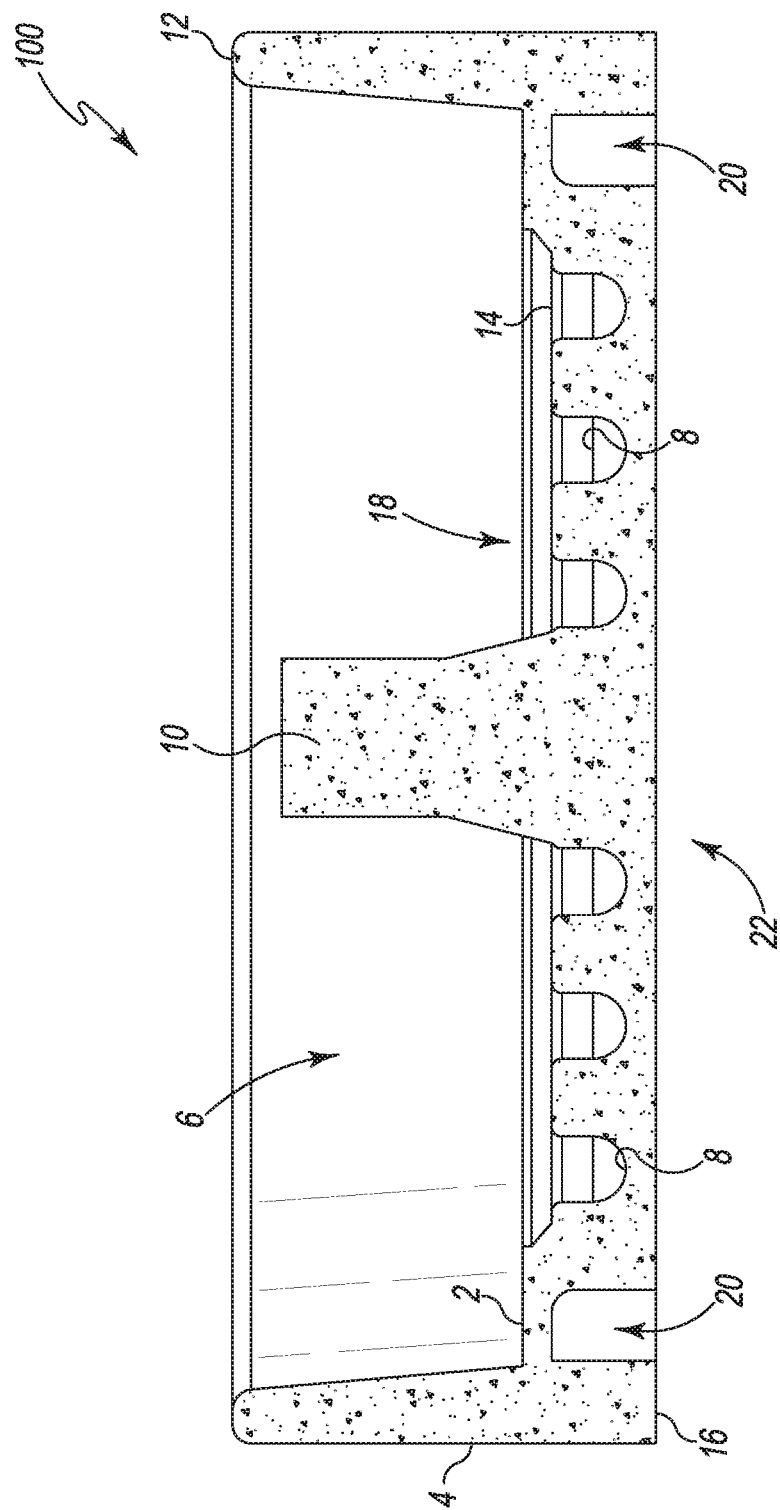
FIG. 2 is a cross-sectional view of the production container.

In one embodiment, the at least one well 8 comprises a wall and a floor, wherein the floor is concave. In one embodiment, the at least one well 8 is shaped like a parabola. Referring to FIGS. 1 and 2, in one embodiment, the production container 100 comprises a plurality of wells 8 having a wall and a concave floor. In some embodiments, the well 8 shape may be amorphous, triangular, square, polygonal, or cone shaped. The wells 8 are configured to culture and form cell micro-tissues. Each well 8 is configured to hold a volume of liquid ranging from about 1 $nL^3$ to about 1 $mL^3$. In one embodiment, the formation section 18 comprises at least 10 wells, at least 20 wells, at least 30 wells, at least 40 wells, at least 50 wells, at least 60 wells, at least 70 wells, at least 80 wells, at least 90 wells, or at least 100 wells. In some embodiments, the wells are made of a biocompatible material that remains stable when autoclaved. In some embodiments, the material is a polymer. In some embodiments, the material is silicone.

In one embodiment, the grip 10 extends outwardly from the formation section 18. In one embodiment, the grip 10 is located at about the center of the formation section 18. In one embodiment, the grip 10 is located off-center in the formation section 18. In some embodiments, the grip 10 is coupled to and extends outwardly from the floor 2. In some embodiments, the grip 10 is configured to be gripped and manipulated by a tool aseptically. In one embodiment, the tool is a pair of forceps. In some embodiments, the grip 10 is configured to be the same height as the top edge 12 of the wall 4. Referring to FIG. 2, in some embodiments, the grip 10 is configured to be shorter than the height of the top edge 12 of the wall 4. In some embodiments, the grip 10 is configured to be taller than the height of the top edge 12 of the wall 4.

The grip 10 is made of a biocompatible material that remains stable when autoclaved. In some embodiments, the grip 10 is made of a polymer. In some embodiments, the grip 10 is made of silicone.

In one embodiment, the production container 100 further comprises a production container channel 20 defined in the bottom surface 22 of the production container 100. In one embodiment, the production container channel 20 is configured to be gripped by a tool. In one embodiment, the tool is a pair of forceps. In one embodiment, the pair of forceps may be placed in contact with the production channel 20 and the bottom edge 16 of the wall 4 to manipulate the production container 100 aseptically.

Figure 3:
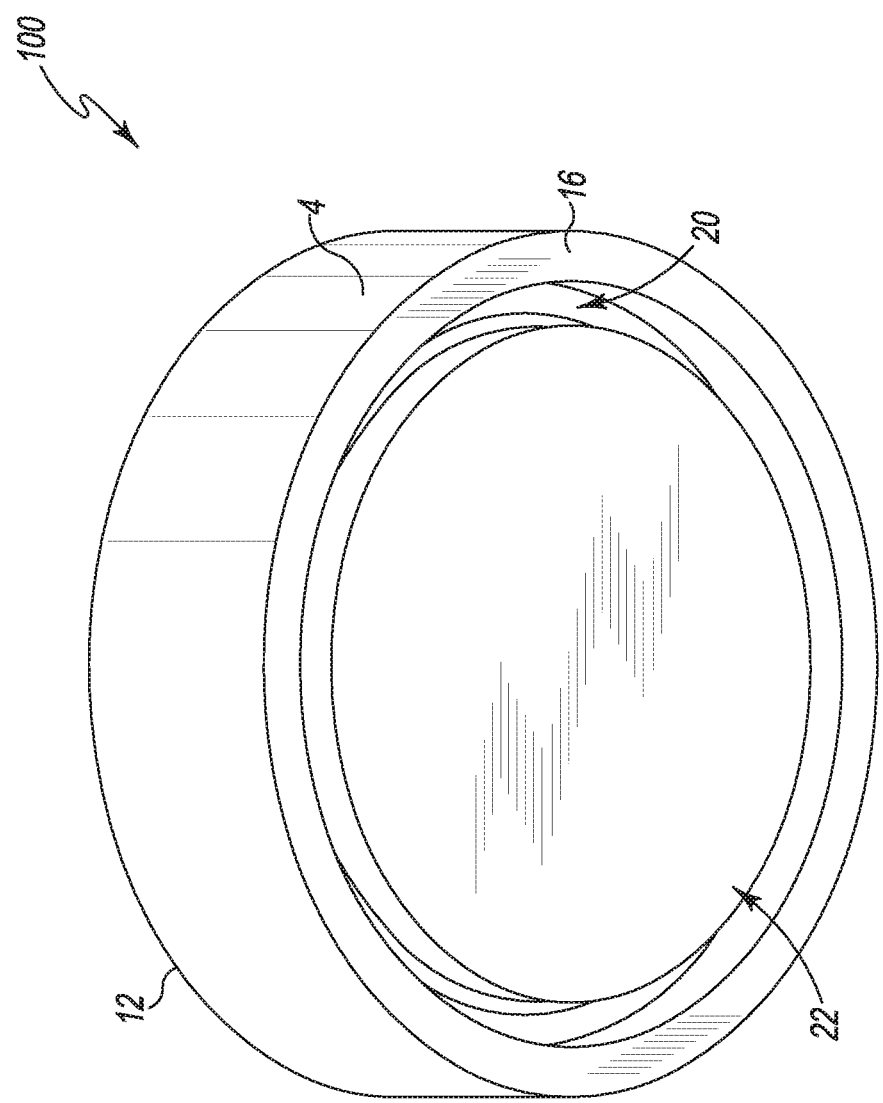
FIG. 3 is a bottom perspective view of the production container.

Referring to FIGS. 2 and 3, in one embodiment, the production container channel 20 is defined in the bottom surface 22 of the production container 100. In one embodiment, the production container channel 20 is defined by bottom edge 16 of the wall 4 and the bottom surface 22. In one embodiment, the production container channel 20 is a continuous and connected channel. In one embodiment, the production container channel 20 mimics the shape of the production container 100. In one embodiment, the production container channel 20 has a depth of about 0.50 mm to about 5 cm. In one embodiment, the production container channel 20 is annular.

The production container 100 is not limited to a single shape. In one embodiment, the production container 100 is shaped annular. Without being limited, the production container 100 may be shaped similar to a polygon, a square, a rectangle, a triangle, a star, or a circle.

In some embodiments, the production container 100 is made of a biocompatible material that remains stable when autoclaved. In one embodiment, the production container 100 is made of a polymer that remains stable when autoclaved. In some embodiments, the production container 100 is made of material that is optically clear. In one embodiment, the material is chosen from a group consisting of glass, metal, polymer, and a combination thereof. In one embodiment, the polymer comprises silicone. In one embodiment, the polymer comprises at least about 95% silicone. In one embodiment, the capture container 100 is made of silicone.

In one embodiment, the production container 100 is configured to fit into the well of a standard six-well plate. Examples of a standard six-well plate is Catalog No. 140675 six-well plate from THERMOFISHER SCIENTIFIC or Manufacture No. 657185 six-well plate from THOMAS SCIENTIFIC, Inc.

In some embodiments, the capture container 200 comprises a capture foundation 24 having a top surface 26 and a bottom surface 28, wherein the top surface 26 defines a conically shaped capture reservoir 30 having a vertex, and the bottom surface 28 defines a capture channel 36, and wherein the capture container 200 is made of a biocompatible material that remains stable when autoclaved.

Figure 4:
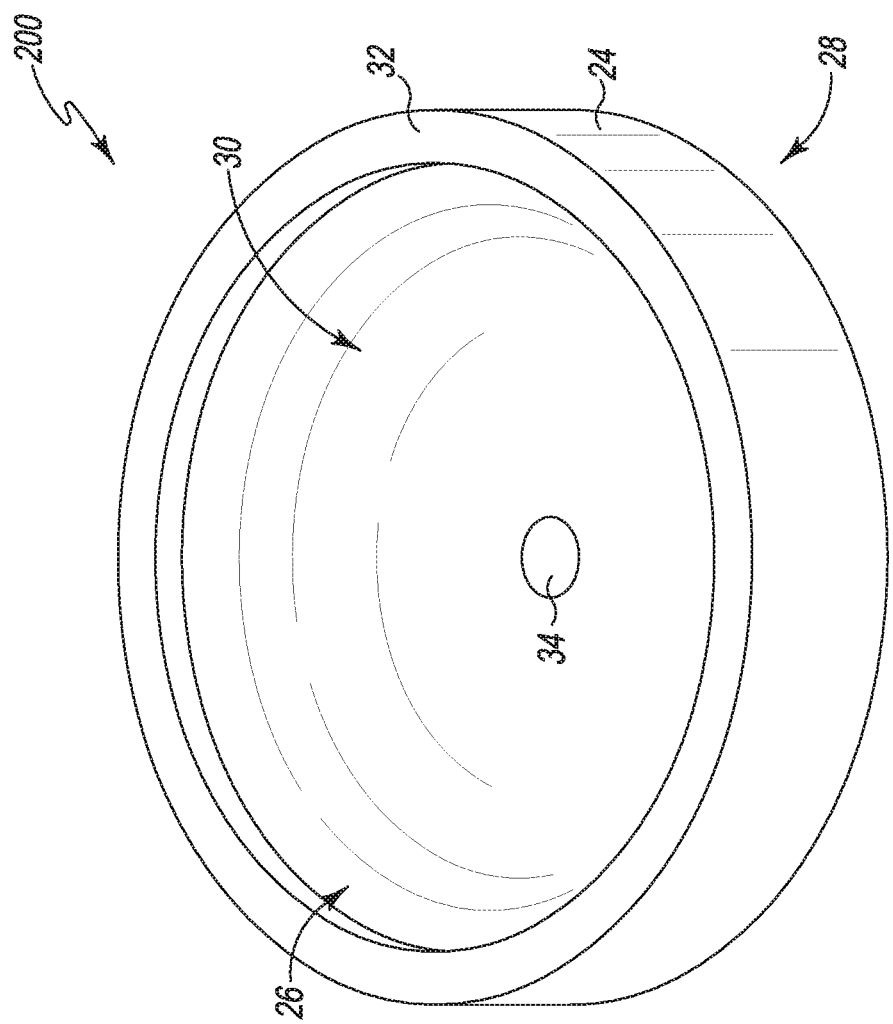
FIG. 4 is a perspective view of a capture container.
Figure 5:
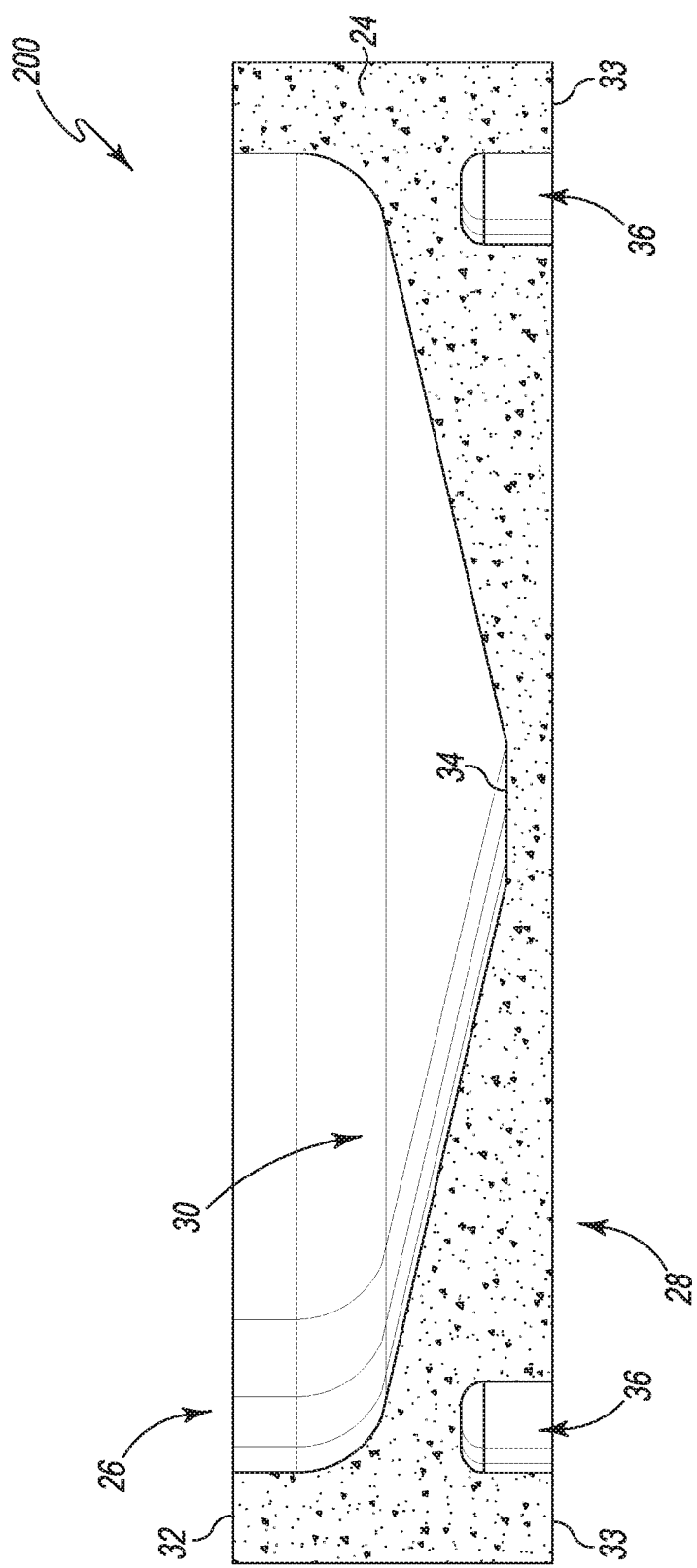
FIG. 5 is a cross-sectional view of the capture container.

Referring now to FIGS. 4 and 5, in one embodiment, the vertex of the capture reservoir 30 comprises a flat surface 34. The flat surface 34 coupled to the conically shaped capture reservoir 30 is configured to capture the cell micro-tissues produced in the production container 100 into a single location. The capture container 200 is configured to be centrifuged to pool the cell micro-tissues onto the flat surface 34.

In one embodiment, the capture channel 36 is defined in the bottom surface 28 of the capture container 200. In one embodiment, the capture container channel 36 is configured to be gripped by a tool. In one embodiment, the tool is a pair of forceps. In one embodiment, the pair of forceps may be placed in contact with the capture container channel 36 and the outer-edge of the capture foundation 24 to manipulate the capture container 200 aseptically.

Referring to FIGS. 4 and 5, in one embodiment, the capture foundation 24 comprises a flat top edge 32 surrounding the capture reservoir 30 and a flat bottom edge 33.

Figure 6:
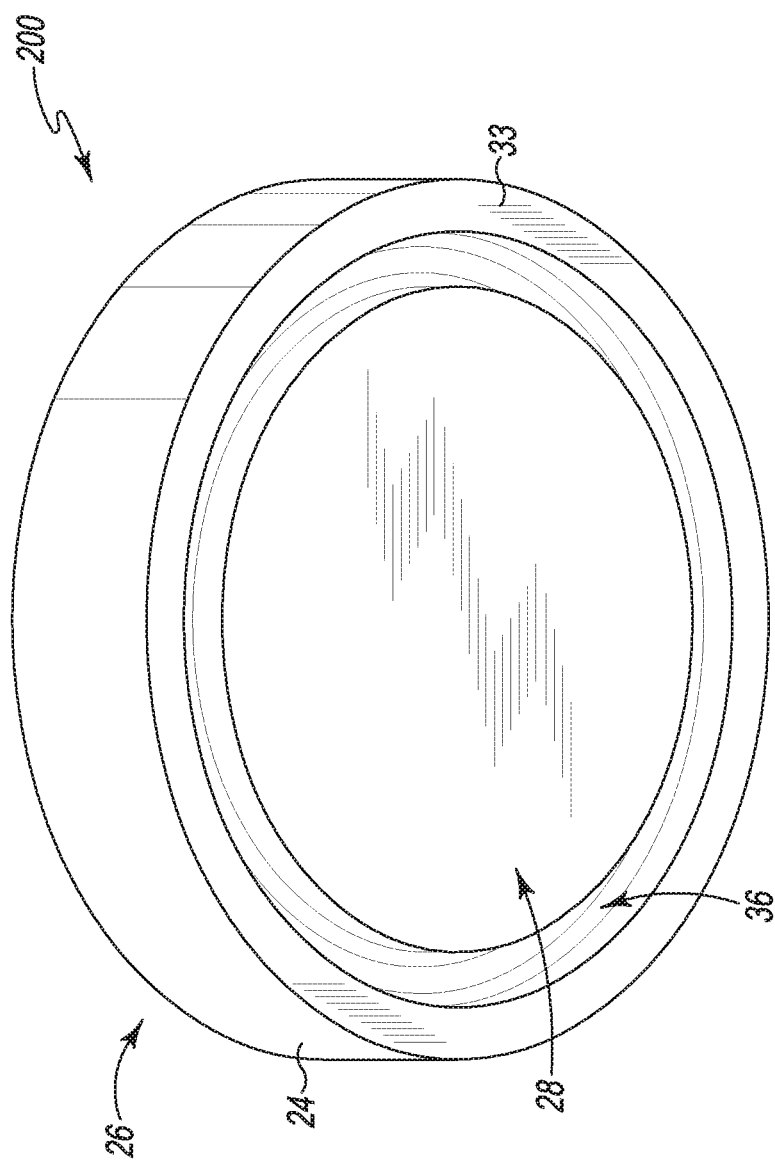
FIG. 6 is a bottom perspective view of the capture container.

Referring to FIGS. 5 and 6, in one embodiment, the capture container channel 36 is defined in the bottom surface 28 of the capture container 200. In one embodiment, the capture container channel 36 is further defined as a channel extending between the flat bottom edge 33 of the capture foundation 24 and the bottom surface 28. In one embodiment, the capture container channel 36 is a continuous and connected channel. In one embodiment, the capture container channel 36 mimics the shape of the capture container 200. In one embodiment, the capture container channel 36 has a depth of about 0.50 mm to about 5 cm. In one embodiment, the capture container channel 36 is annular.

The capture container 200 is not limited to a single shape. In one embodiment, the capture container 200 has an annular shape. Without being limited, the capture container 200 may be shaped similar to a polygon, a square, a rectangle, a triangle, a star, or a circle.

The capture container 200 is made of a biocompatible material that remains stable when autoclaved. In one embodiment, the capture container 200 is made of a polymer that remains stable when autoclaved. In one embodiment, the capture container 200 is made of a material that is optically clear. In one embodiment, the material is chosen from a group consisting of glass, metal, polymer, and a combination thereof. In one embodiment, the polymer comprises silicone. In one embodiment, the polymer comprises at least about 95% silicone. In one embodiment, the capture container 200 is made of silicone.

In one embodiment, the capture container 200 is configured to fit into the well of a standard six-well plate. Examples of a standard six-well plate is Catalog No. 140675 six-well plate from THERMOFISHER SCIENTIFIC or Manufacture No. 657185 six-well plate from THOMAS SCIENTIFIC, Inc.

The micro-tissue production component comprises the production container 100 and the capture container 200. In one embodiment, the micro-tissue production component comprises (i) a production container 100 comprising a floor 2, a wall 4 extending from the floor 2, wherein the floor 2 and wall 4 define a production reservoir 6, and wherein the wall 4 includes a top edge 12. The production container further comprising a formation section 18 defined in the floor 2, wherein the formation section 18 comprises at least one well 8, a grip 10 extending outwardly from the formation section 18. The micro-tissue production component further comprising (ii) a capture container 200, comprising a capture foundation 24 having a top surface 26 and a bottom surface 28, wherein the top surface 26 defines a conically shaped capture reservoir 30, and the bottom surface 28 defines a capture channel 36, and wherein the top edge 12 of the production container 100 is positioned to contact the top surface 26 of the capture container 200.

In one embodiment, the micro-tissue production component comprises the production container 100 having a top edge 12 positioned to contact the flat top edge 32 of the capture container 200. In some embodiments, the production container 100 is aseptically manipulated to contact the capture container 200. In this configuration, the cell microtissues from the production container 100 may be captured in the capture container 200.

In some embodiments, the micro-tissue production component is configured to be centrifuged. In some embodiments, the production container 100 is configured to fit like a lid over the capture container 200, and wherein the wall 4 of the production container 100 externally surrounds the capture container 200.

In one embodiment, the micro-tissue production component comprises the production container 100 configured to be positioned over the capture container 200 such that, when centrifuged, microtissues from the formation section 18 and the wells 8 are forced into the reservoir 30 of the capture container 200, facilitating aseptic manipulation of the microtissues with a fluid handling device. An example of a fluid handling device is a pipettor. In some embodiments, the microtissues are aseptically removed from the capture container 200 by use of a fluid handling device. An example of a fluid handling device is a pipette.

In one embodiment, the micro-tissue production component may be cleaned after use by filing the production container 100 and the capture container 200 with 70% ethanol and aspirated or centrifuged to remove all liquids. In some embodiments, the production container 100 and capture container 200 are washed with a PBS solution before or after the ethanol wash. The component reservoirs (6 and 30) are then filled with 3% hydrogen peroxide solution and a platinum disk is placed into the reservoir (6 or 30). The hydrogen peroxide and platinum disk are available together in contact lens cleaning kits from local grocers. If needed, the production container 100 can be centrifuged to force the hydrogen peroxide into the wells 8. The hydrogen peroxide-platinum disk should incubate for about 3-6 hours to remove cell debris from the wells 8. Following incubation, the micro-tissue production component is rinsed with water (centrifuged, if need be), dried, and autoclaved. In one embodiment, the micro-tissue production component is autoclaved for at least about 15 minute sterilization cycle at about 121 deg C. In some embodiments, the autoclave step further includes at least about a 5 minute dry cycle. After the micro-tissue production component has cooled, the production container 100 and capture container 200 are ready for use.

The biofabrication system comprises a micro-tissue production component, a perfusible tissue formation component 600, and a bioreactor 700. In some embodiments, the perfusible tissue formation component 600 comprises a platen 300 and an undercast 400. The perfusible tissue formation component 600 is configured to form a perfusible tissue construct 102. The perfusible tissue formation component 600 is made of a biocompatible material that remains stable when autoclaved. In some embodiments, the platen 300 and undercast 400 are configured to couple together. In some embodiments, the perfusible tissue formation component 600 comprises the platen 300 and a small undercast 500. In some embodiments, the platen 300 and the small undercast 500 are coupled together.

The platen 300 comprises a top surface 38 having a conically shaped platen reservoir 40, wherein the platen reservoir 40 comprises a vertex having a porous section 42 comprising a flat surface 44 and at least one opening 46. In one embodiment, a flat outer edge 48 surrounds the conically shaped platen reservoir 40. The platen 300 further comprises a bottom surface 52 defining a platen channel 56. The platen 300 is made of a biocompatible material that remains stable when autoclaved.

Figure 7:
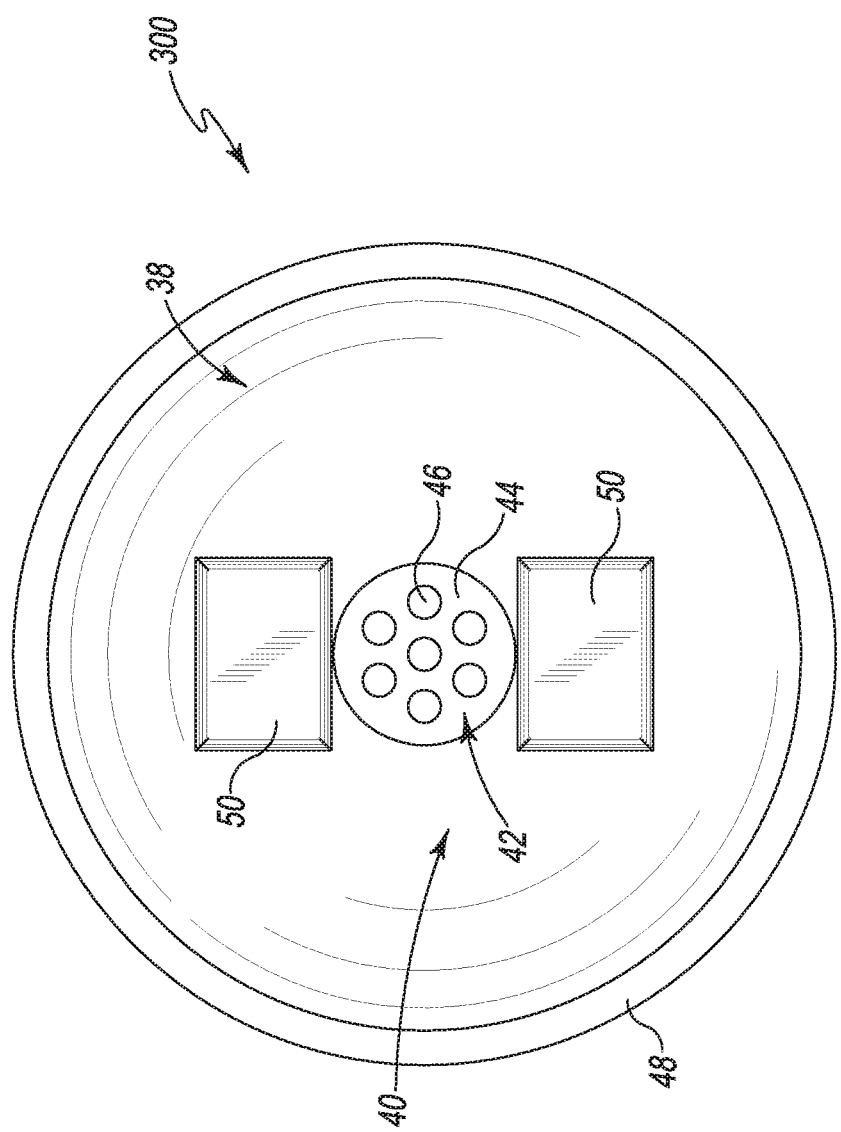
FIG. 7 is a top view of a platen.
Figure 8:
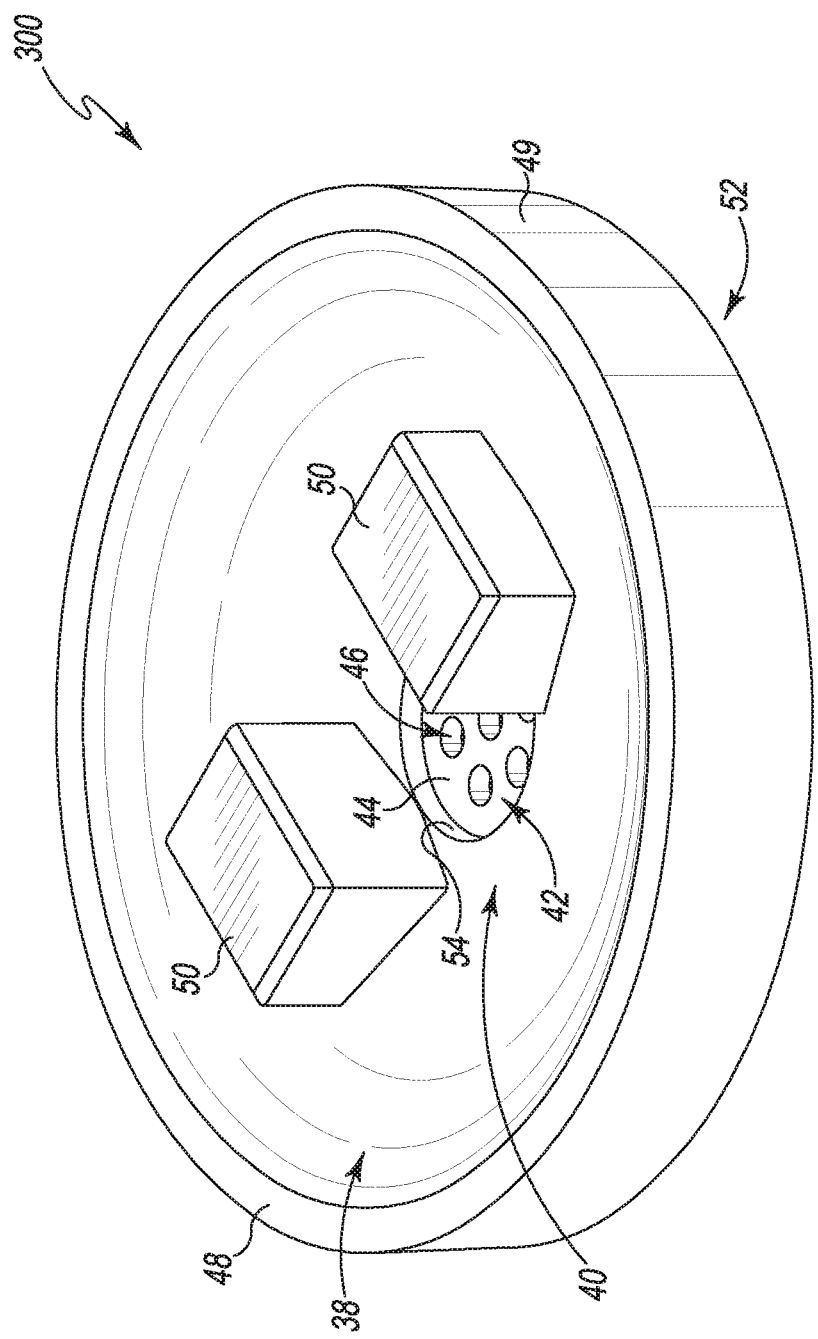
FIG. 8 is a perspective view of the platen.

Referring now to FIGS. 7 and 8, in one embodiment, the platen 300 comprises a platen foundation 49 having a top surface 38 and a bottom surface 52. The top surface 38 comprises a conically shaped platen reservoir 40 having a vertex. The vertex comprises a porous section 42 having a porous section wall 54, a flat surface 44, and at least one opening 46. The top surface 38 further comprises a flat outer edge 48 that surrounds the platen reservoir 40. At least one grip 50 is coupled to and extends outwardly from the top surface 38. In some embodiments, the platen 300 comprises at least two grips 50 coupled to the top surface.

In some embodiments, the grip 50 is coupled to the top surface 38. In some embodiments, the grip 50 is coupled the top surface located between the porous section 42 and the flat outer edge 48. The grip 50 is configured to be gripped by a tool to manipulate the platen 300 aseptically. In some embodiments, the tool is a pair of forceps. In some embodiments, the grip 50 is configured to be taller than the flat outer edge 48 of the platen 300. In some embodiments, the grip 50 is configured to be the same height as the flat outer edge 48.

Figure 10:
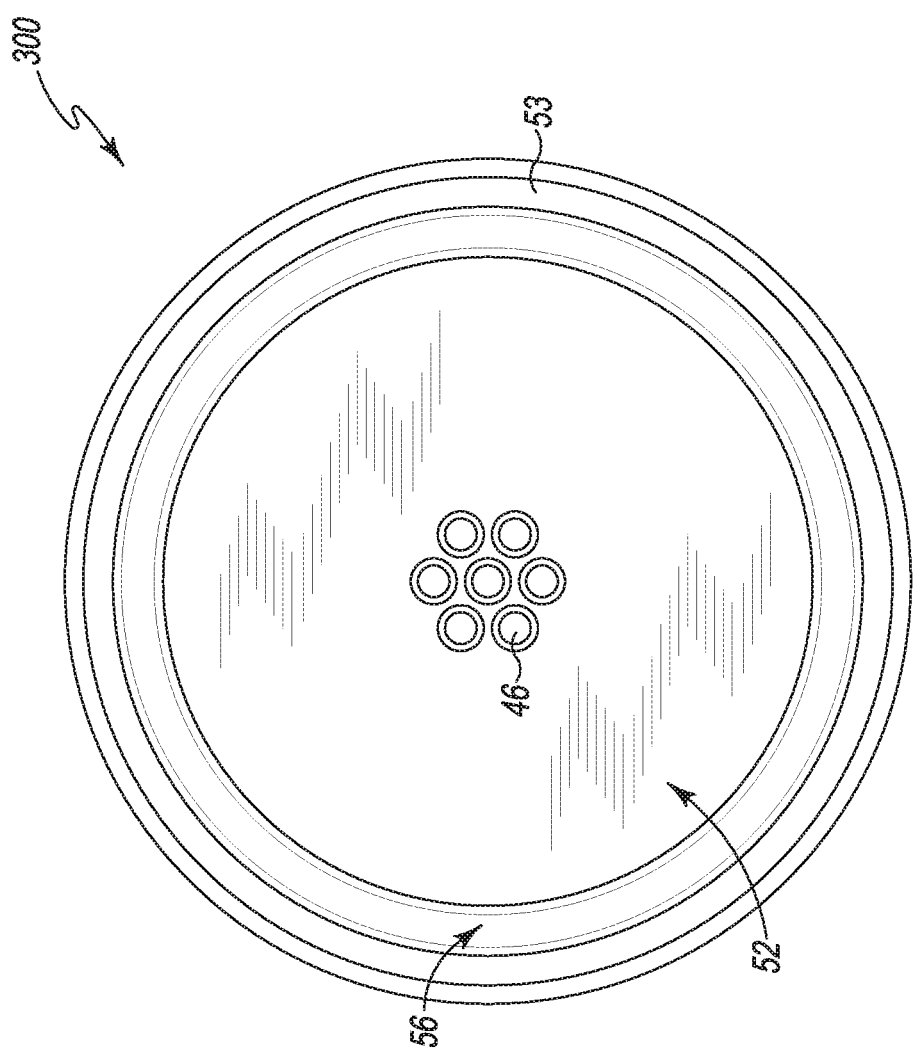
FIG. 10 is a bottom view of the platen.

Referring to FIGS. 7, 8, and 10, in one embodiment, the platen 300 comprises a porous section 42 comprising a flat surface 44 and at least one opening 46. In some embodiments, the porous section 42 further comprises a porous section wall 54. In some embodiments, the porous section 42 is located at the vertex of the conically shaped reservoir 40. The at least one opening 46 traverses through the platen 300. In some embodiments, the porous section 42 comprises a plurality of openings 46. A person of skill in the art will recognize that the porous section may be configured with any number of openings 46. In some embodiments, the porous section comprises at least one opening, at least two openings, at least three openings, at least four openings, at least five openings, at least six openings, at least seven openings, at least eight openings, at least nine openings, at least ten openings, at least fifteen openings, at least twenty openings, or at least 25 openings.

A person having skill in the art will recognize that the size of the at least one opening 46 will vary depending on the desired pore size in the perfusible tissue construct 102. In some embodiments, the opening is a circle. In some embodiments, the opening has the shape of a square, rectangle, polygon, star, triangle, or amorphous. In some embodiments the diameter of the opening is about 0.01 cm to about 7 cm.

A person having skill in the art will recognize that the pattern of the at least one opening 46 may be generated as desired by the person having skill in the art's preferred location for generated pores in the perfusible-tissue construct 102.

In some embodiments, the porous section is configured to couple with at least one member 72 of the undercast 400, described further below. In some embodiments, the cell micro-tissues captured in the capture container 200 are placed in the porous section 42 of the platen 300. In some embodiments, the cell micro-tissues assemble around the at least one member 72 and fuse to each other to generate a perfusible tissue construct 102 when the undercast 400 is removed and the space left by the at least one member 72 forms a perfusible opening contiguous with the at least one opening 46 of the platen 300. In this embodiment, the shape, size, pattern, and number of the at least one opening 46 will be limited by the shape, size, and number of the at least one member 72 of the under cast 400.

In some embodiments, the porous section 42 comprises a mesh screen (not shown). In this embodiment, the mesh screen is coupled to the porous section 42, and the opening 46 of the platen 300. Additionally, in this embodiment, the platen 300 comprising a porous section 42 comprising a mesh screen would not couple to an undercast 400 or small undercast 500 (as described later below). The cell microtissues placed on top of the mesh screen will form a perfusible tissue construct 102 based on the natural porosity generated from the piled micro-tissues. In this embodiment, the pores in the perfusible tissue construct 102 are random rather than controlled.

In some embodiments, the pores of the mesh screen have a diameter of about 10 micrometers to about 5,000 micrometers. In some embodiments, the mesh screen has a diameter of about 0.050 millimeters to about 40 millimeters.

Figure 9:
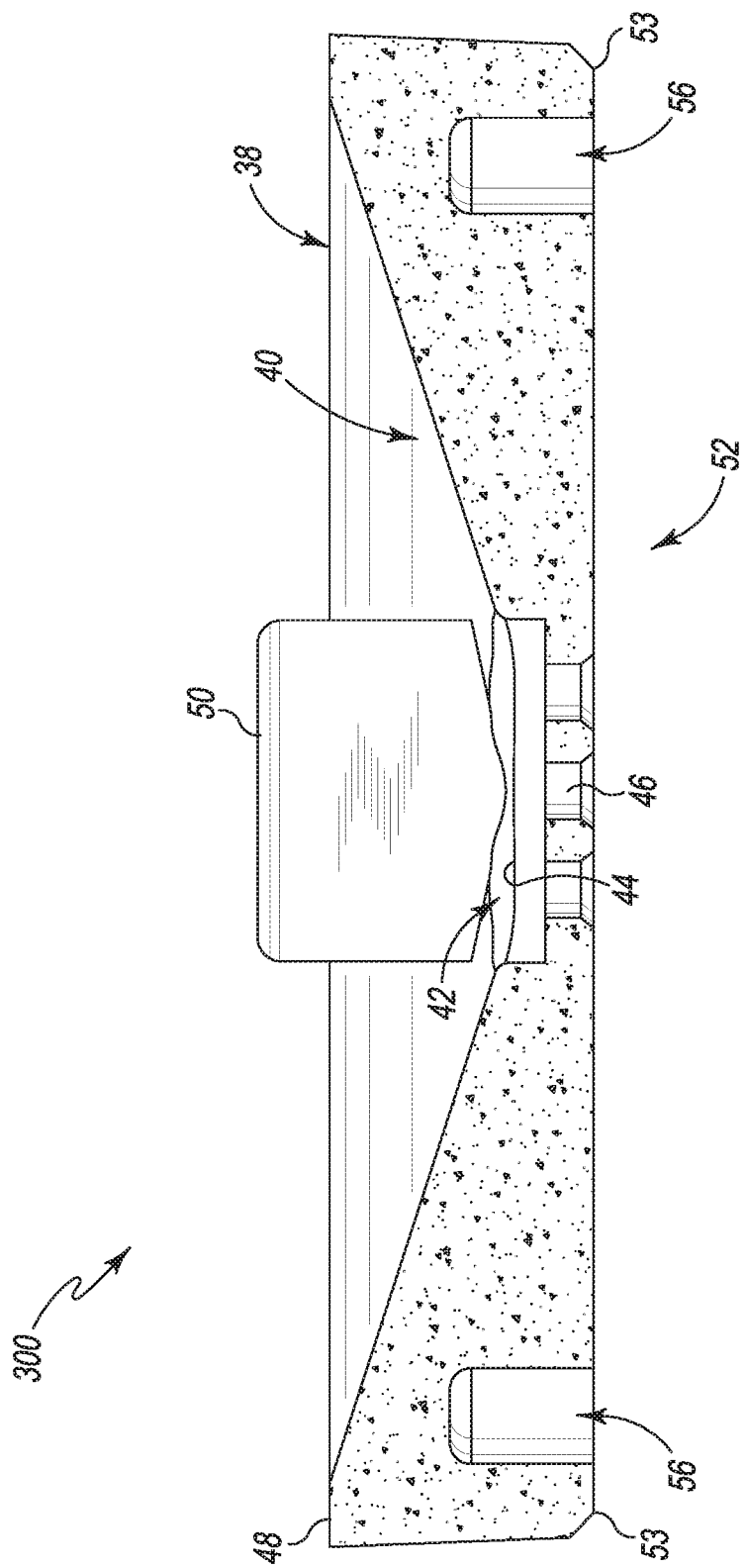
FIG. 9 is a cross-sectional view of the platen.

Referring to FIGS. 9 and 10, the platen 300 further comprises a bottom surface 52 having a platen channel 56 defined therein. In some embodiments, the bottom surface 52 further comprises an outer edge 53. In some embodiments, the platen channel 56 is defined by the outer edge 53 and the bottom surface 52 of the platen 300. In one embodiment, the platen channel 56 is configured to be gripped by a tool. In one embodiment, the tool is a pair of forceps. In one embodiment, the pair of forceps may be placed in contact with the platen channel 56 and the outer edge 53 of the bottom surface 52 to manipulate the platen 300 aseptically. Additionally, the platen channel 56 is configured to receive a grip insert 68 of the undercast 400 as described in more detail below. In some embodiments, the platen channel 56 further comprises a relief valve to reduce air bubbles when the platen channel 56 is in contact with another component (not shown). In some embodiments, the relief valve includes an opening in fluid communication between platen channel 56 and the top surface 38 so that air can escape from the platen channel 56.

In one embodiment, the platen channel 56 is a continuous and connected channel. In one embodiment, the platen channel 56 mimics the shape of the platen 300. In one embodiment, the production platen channel 56 has a depth of about 0.50 mm to about 5 cm. In one embodiment, the platen channel 56 is annular.

In some embodiments, the platen 300 is not limited to a single shape. In one embodiment, the platen 300 has an annular shape. Without being limited, the platen 300 may be shaped similar to a polygon, a square, a rectangle, a triangle, a star, or a circle.

The platen 300 is made of a biocompatible material that remains stable when autoclaved. In one embodiment, the platen 300 is made of a polymer that remains stable when autoclaved. In one embodiment, the platen 300 is made of a material that is optically clear. In one embodiment, the material is chosen from a group consisting of glass, metal, polymer, and a combination thereof. In one embodiment, the polymer comprises silicone. In one embodiment, the polymer comprises at least about 95% silicone. In one embodiment, the platen 300 is made of silicone.

In one embodiment, the platen 300 is configured to fit into the well of a standard six-well plate. Examples of a standard six-well plate is Catalog No. 140675 six-well plate from THERMOFISHER SCIENTIFIC or Manufacture No. 657185 six-well plate from THOMAS SCIENTIFIC, Inc.

In some embodiments, the perfusible tissue component 600 comprises a platen 300 and an undercast 400. The undercast 400 comprises a floor 58 having at least one relief port 60 and a wall 62 extending outwardly from the floor 58. The undercast 400 further comprises a perfusible-formation section 66 defined by a grip insert 68 surrounding a platform 70 and at least one member 72. In some embodiments, the at least one member 72 extends outwardly from the platform 70. In some embodiments, the perfusible-formation section 66 is coupled to the floor 58. In some embodiments, the undercast 400 further comprises an undercast channel 64 defined by the floor 58, the wall 62, and the grip insert 68. In some embodiments, the undercast channel 64 extends between the wall 62 and the perfusible-formation section 66. In some embodiments, the undercast channel 64 is annular. In some embodiments, the undercast channel 64 is continuous. In some embodiments, the undercast channel 64 mimics the shape of the undercast 400.

Figure 11:
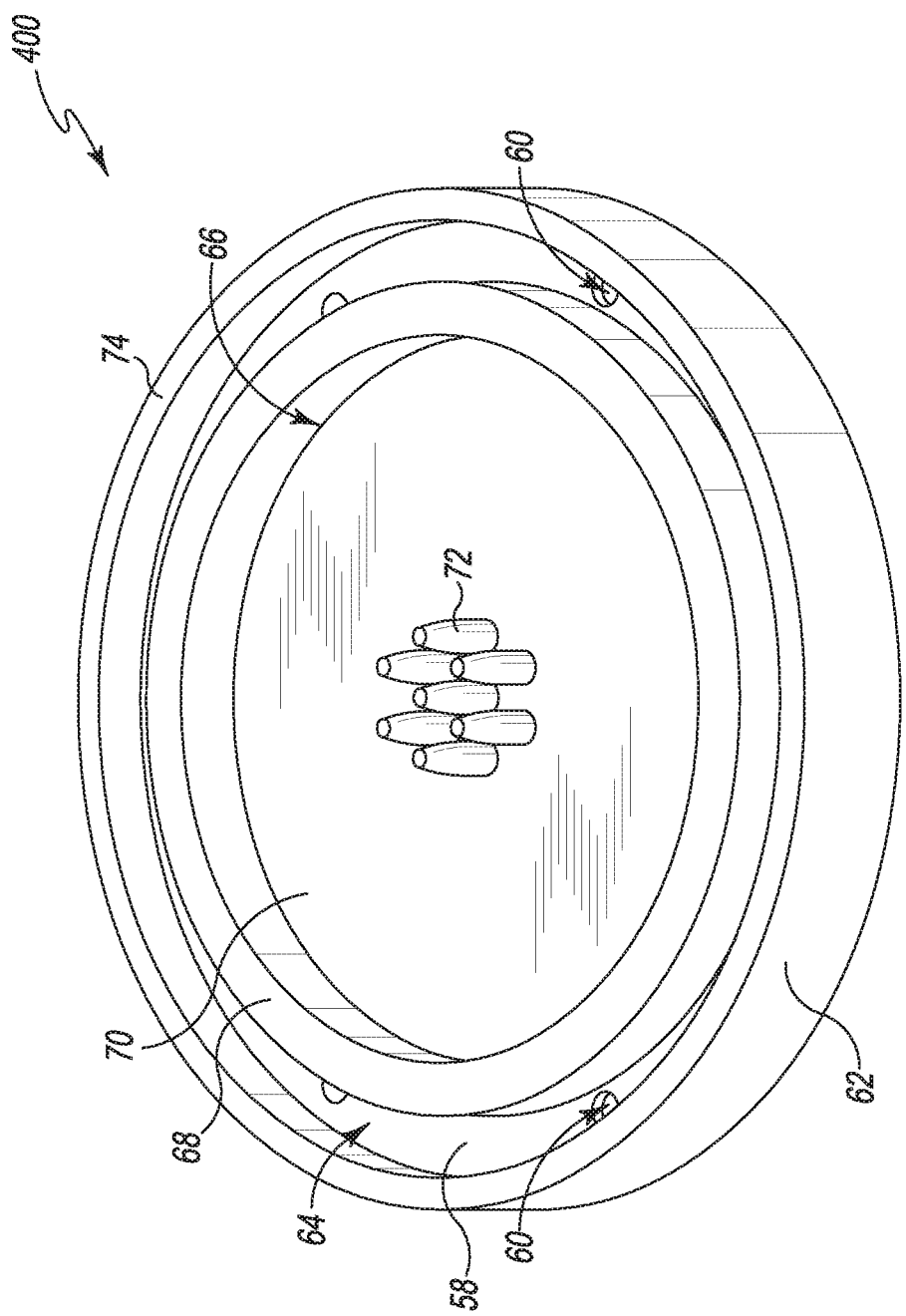
FIG. 11 is a perspective view of an undercast.
Figure 12:
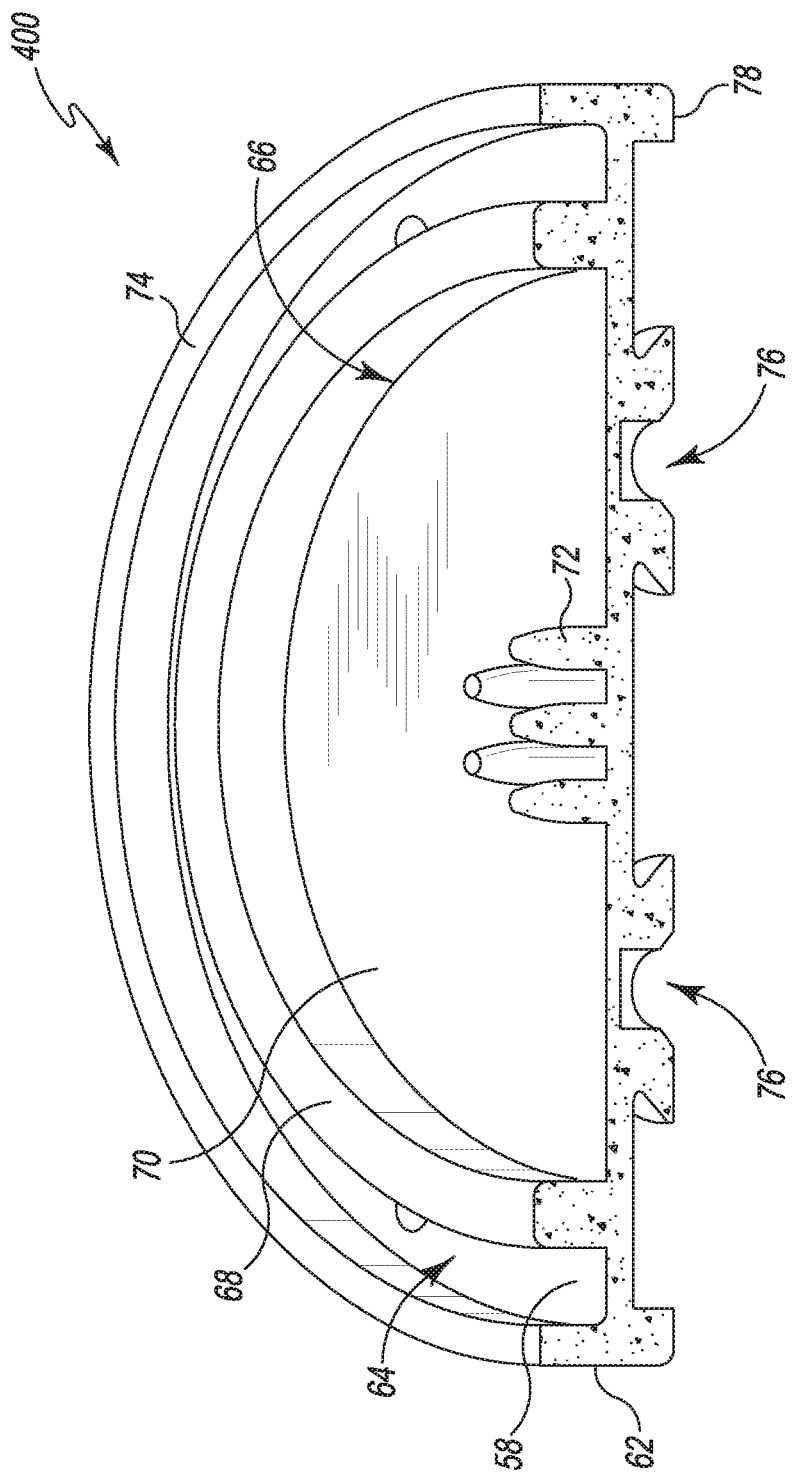
FIG. 12 is a cross-sectional view of the undercast.
Figure 13:
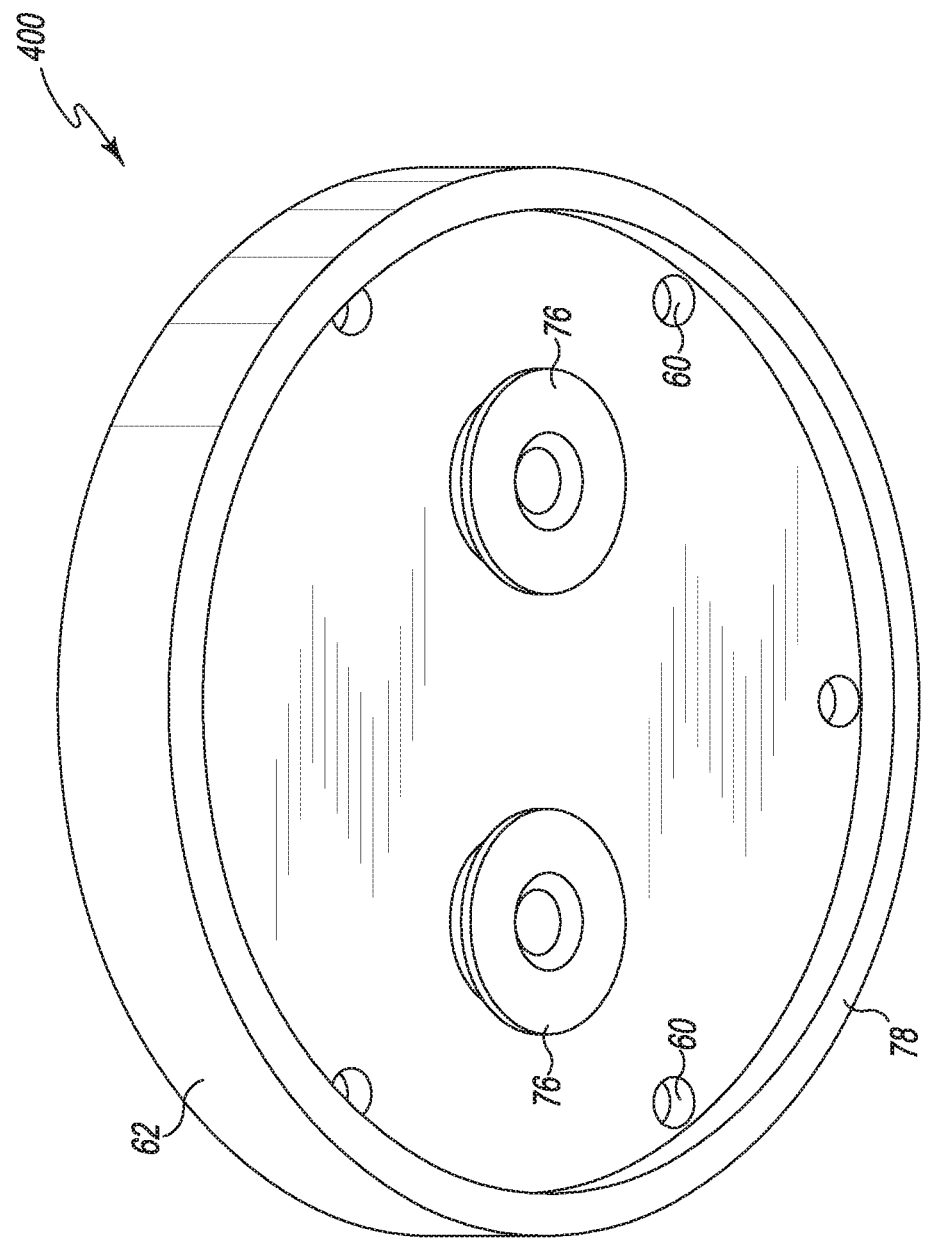
FIG. 13 is a bottom perspective of the undercast.

Referring now to FIGS. 11, 12, and 13, in some embodiments, the undercast 400 comprises a wall 62 having a top edge 74 and a bottom edge 78. In some embodiments, the top edge 74 is configured to be gripped by a tool to manipulate the undercast 400 aseptically. In some embodiments, the tool is a pair of forceps. In some embodiments, the grip insert 68 is configured to couple to the platen channel 56. In some embodiments, the platen channel 56 is positioned to receive the grip insert 68 of the undercast 400.

In some embodiments, the undercast 400 further comprises an underside grip 76. In some embodiments, the underside grip 76 is coupled to and extending outwardly from the platform 70 of the undercast 400. In some embodiments, the undercast 400 comprises two underside grips 76 coupled to and extending outwardly from the platform 70.

In some embodiments, the at least one member 72 is selected from a group consisting of a tine, a post, and a cone. The size, shape, pattern, and number of the at least one member 72 will depend on the desired number, size, and location of pores to be produced in the perfusible-tissue construct 102. A person of skill in the art will recognize that the formation section 66 may be configured with any number of at least one members 72. In some embodiments, the formation section 66 comprises at least one member, at least two members, at least three members, at least four members, at least five members, at least six members, at least seven members, at least eight members, at least nine members, at least ten members, at least fifteen members, at least twenty members, or at least 25 members.

In some embodiments, the at least one member 72 has a bottom circumference of about 10 micrometers to about 5,000 micrometers, and a top circumference of about 10 micrometers to about 5,000 micrometers. In some embodiments, the at least one member 72 has a bottom circumference of at least 10 micrometers, at least 20 micrometers, at least 30 micrometers, at least 40 micrometers, at least 50 micrometers, at least 60 micrometers, at least 70 micrometers, at least 80 micrometers, at least 90 micrometers, or at least 100 micrometers. In some embodiments, the at least one member 72 has a bottom circumference of about 100 micrometers, about 200 micrometers, about 300 micrometers, about 400 micrometers, about 500 micrometers, about 600 micrometers, about 700 micrometers, about 800 micrometers, about 900 micrometers, or about 1,000 micrometers. In some embodiments, the bottom circumference of the at least one member 72 ranges from about 500 micrometers to about 1,000 micrometers, about 1,000 micrometers to about 1,500 micrometers, about 1,500 micrometers to about 2,000 micrometers, about 2,000 micrometers to about 2,500 micrometers, about 2,500 micrometers, to about 3,000 micrometers, about 3,000 micrometers to about 3,500 micrometers, about 3,500 micrometers to about 4,000 micrometers, about 4,000 micrometers to about 4,500 micrometers, or about 4,500 micrometers to about 5,000 micrometers.

A person having skill in the art will recognize that the size (including height, width, or circumference) of the at least one member 72 will vary depending on the desired pore size in the perfusible tissue construct 102. In some embodiments, the at least one member 72 is round. In some embodiments, the at least one member 72 has the shape of a square, rectangle, polygon, star, triangle, or amorphous. In some embodiments the diameter of the at least one member 72 is about 0.01 cm to about 3 cm.

A person having skill in the art will recognize that the pattern of the at least one member 72 may be generated as desired by the person's having skill in the art preferred location for generated pores in the perfusible-tissue construct 102.

In some embodiments, the at least one member 72 of the undercast 400 is configured to couple with at least one opening 46 of the platen 300, described further below. In some embodiments, the cell micro-tissues captured in the capture container 200 are placed in the porous section 42 of the platen 300. In some embodiments, the cell micro-tissues assemble around the at least one member 72 and fuse to each other to generate a perfusible tissue construct 102 when the undercast 400 is removed and the space left by the at least one member 72 forms a perfusible opening contiguous with the at least one opening 46 of the platen 300. In this embodiment, the shape, size, pattern, and number of the at least one member 72 will be limited by the shape, size, and number of the at least one opening 46 of the platen 300.

In some embodiments, the at least one member 72 is positioned to traverse the at least one opening 46 of the platen 300. In some embodiments, the at least one member 72 comprises a material to prevent cell adhesion. In some embodiments, the at least one member 72 is coated with a material to prevent cell adhesion. Examples of a material to prevent cell adhesion are silicone, polyHEMA, and agarose.

In some embodiments, the undercast 400 is not limited to a single shape. In one embodiment, the undercast 400 has an annular shape. Without being limited, the undercast 400 may be shaped similar to a polygon, a square, a rectangle, a triangle, a star, or a circle.

The undercast 400 is made of a biocompatible material that remains stable when autoclaved. In one embodiment, the undercast 400 is made of a polymer that remains stable when autoclaved. In some embodiments, the undercast 400 is made of a material that is optically clear. In one embodiment, the material is chosen from a group consisting of ceramic, glass, metal, polymer, and a combination thereof. In one embodiment, the polymer comprises resin. In one embodiment, the polymer comprises at least about 95% resin. In one embodiment, the undercast 400 is made of a resin. In some embodiments, the undercast 400 is made of Filtek Silorane. In one embodiment, the undercast 400 is made of a polymer except the at least one member 72 is made of a resin. In some embodiments, the undercast 400 is made of A2 Resin. In one embodiment, the undercast 400 is comprises Silorane except the at least one member 72 comprises A2 resin. In one embodiment, the undercast 400 is made of Silorane except the at least one member 72 are made of A2 resin.

In one embodiment, the undercast 400 is configured to fit into the well of a standard six-well plate. Examples of a standard six-well plate is Catalog No. 140675 six-well plate from THERMOFISHER SCIENTIFIC or Manufacture No. 657185 six-well plate from THOMAS SCIENTIFIC, Inc.

Figure 16:
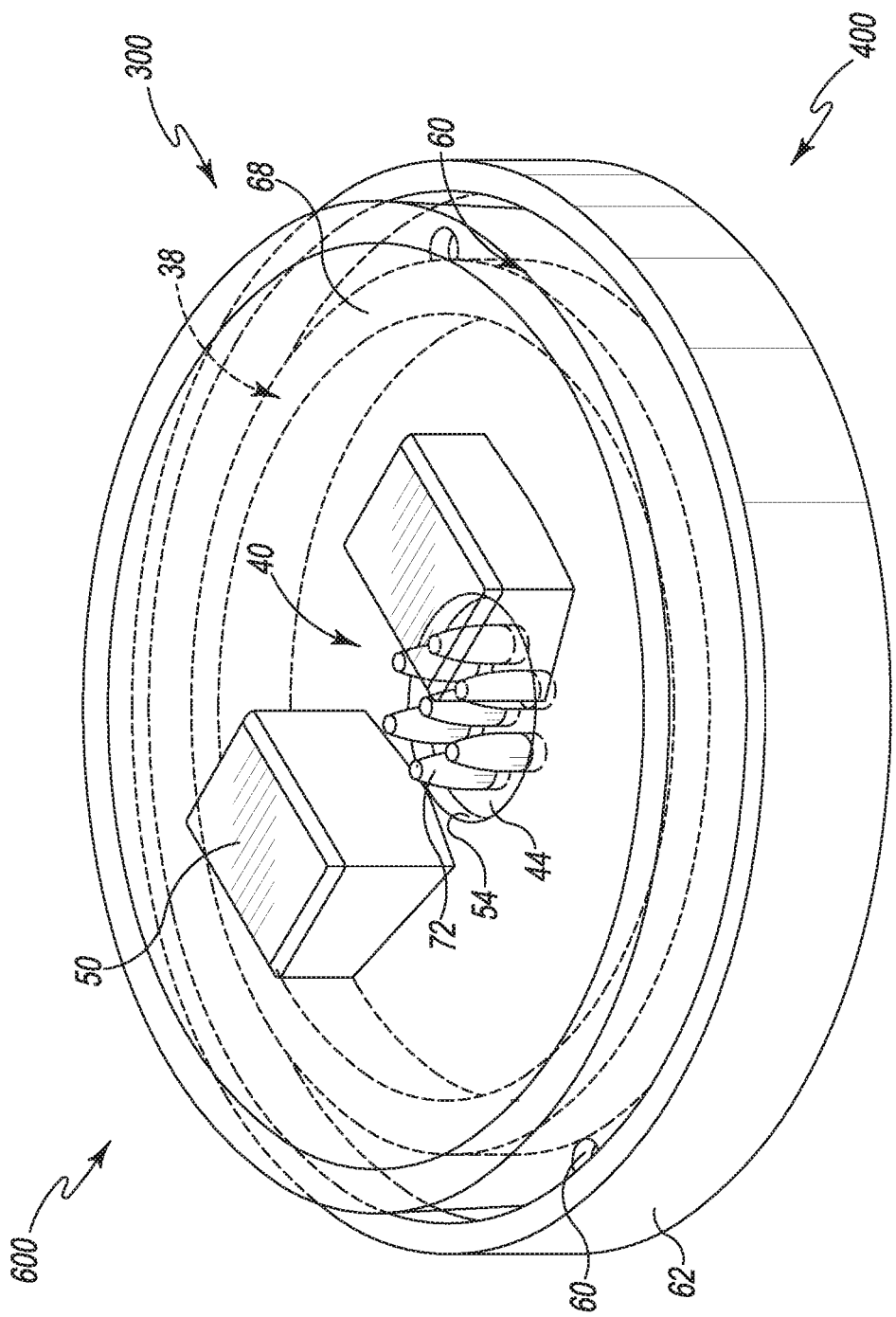
FIG. 16 is a perspective view of a platen coupled to an undercast.
Figure 17:
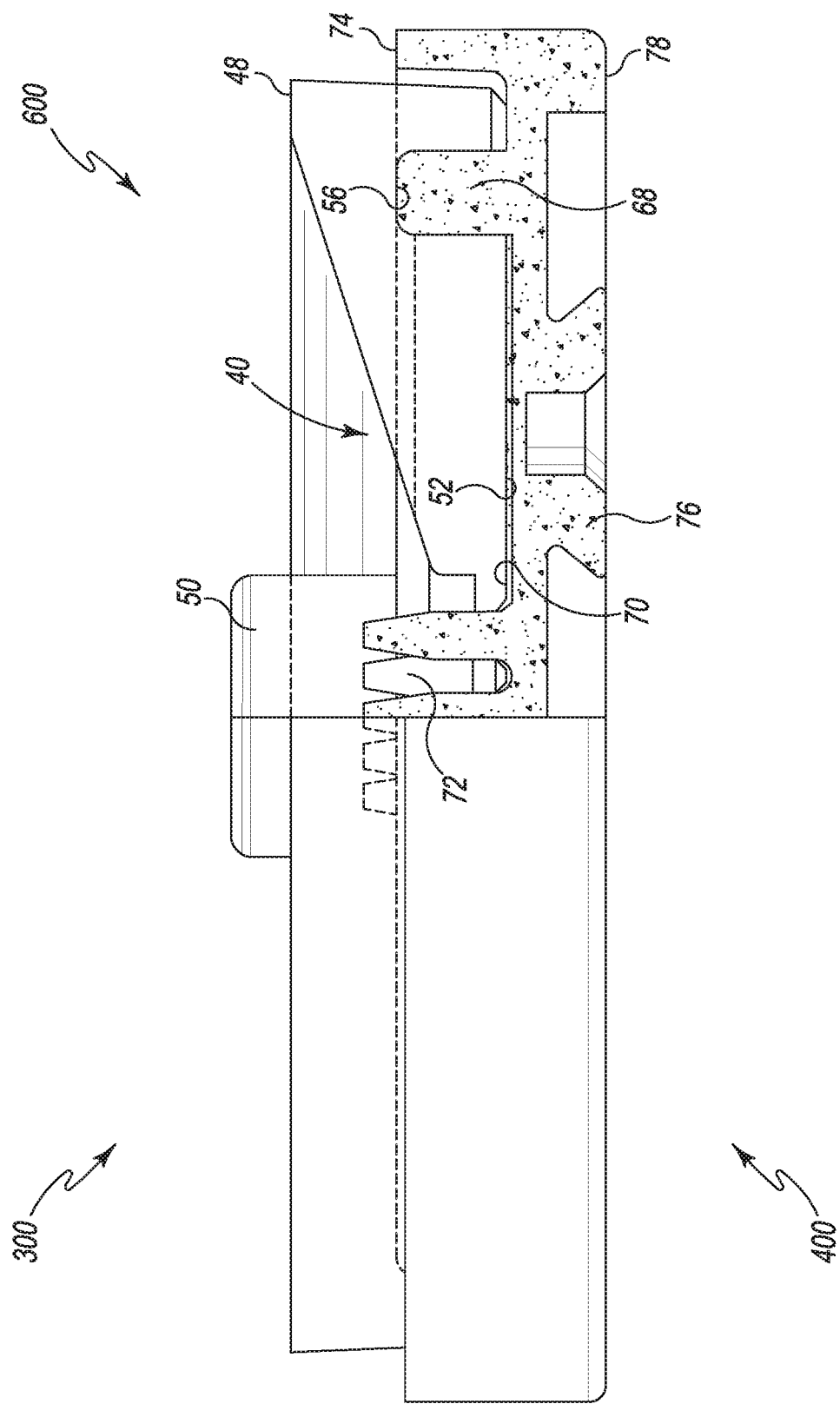
FIG. 17 is a partial side sectional view of a platen coupled to an undercast.

Referring now to FIGS. 16 and 17, in some embodiments, a perfusible-tissue formation component 600 comprises a platen 300 and an undercast 400. In some embodiments, the undercast 400 is configured to receive the platen 300. Specifically, in some embodiments, the at least one member 72 is positioned to traverse the at least one opening 46 of the platen 300, and the platen channel 56 is positioned to receive the grip insert 68 of the undercast 400. In some embodiments, the undercast channel 64 is positioned to receive the outer edge 53 of the platen 300.

In some embodiments, the perfusible-tissue formation component 600 comprises (i) an undercast 400 comprising: a floor 58 having at least one relief port 60; a wall 62 extending outwardly from the floor 58; a perfusible-formation section 66 defined by a grip insert 68 surrounding a platform 70, and at least one member 72, wherein the at least one member 72 extends outwardly from the platform 70, wherein the perfusible-formation section 66 is coupled to the floor 58, and wherein an undercast channel 64 defined by the floor 58, the wall 62, and the grip insert 68 extends between the wall 62 and the perfusible-formation section 66; and (ii) a platen 300 comprising: a top surface 38 having a conically shaped platen reservoir 40, wherein the platen reservoir 40 comprises a vertex locating the porous section 42, wherein the porous section 42 comprises a flat surface 44 and at least one opening 46, and a bottom surface 52 defining a platen channel 56; wherein the platen channel 56 is positioned to receive the grip insert 68 of the undercast 400, and the at least one member 72 traverses the at least one opening 46; and wherein the perfusible-tissue formation component 600 is made of a biocompatible material that remains stable when autoclaved.

In some embodiments, the perfusible-tissue formation component 600 comprises a platen 300 and a small undercast 500.

Figure 14:
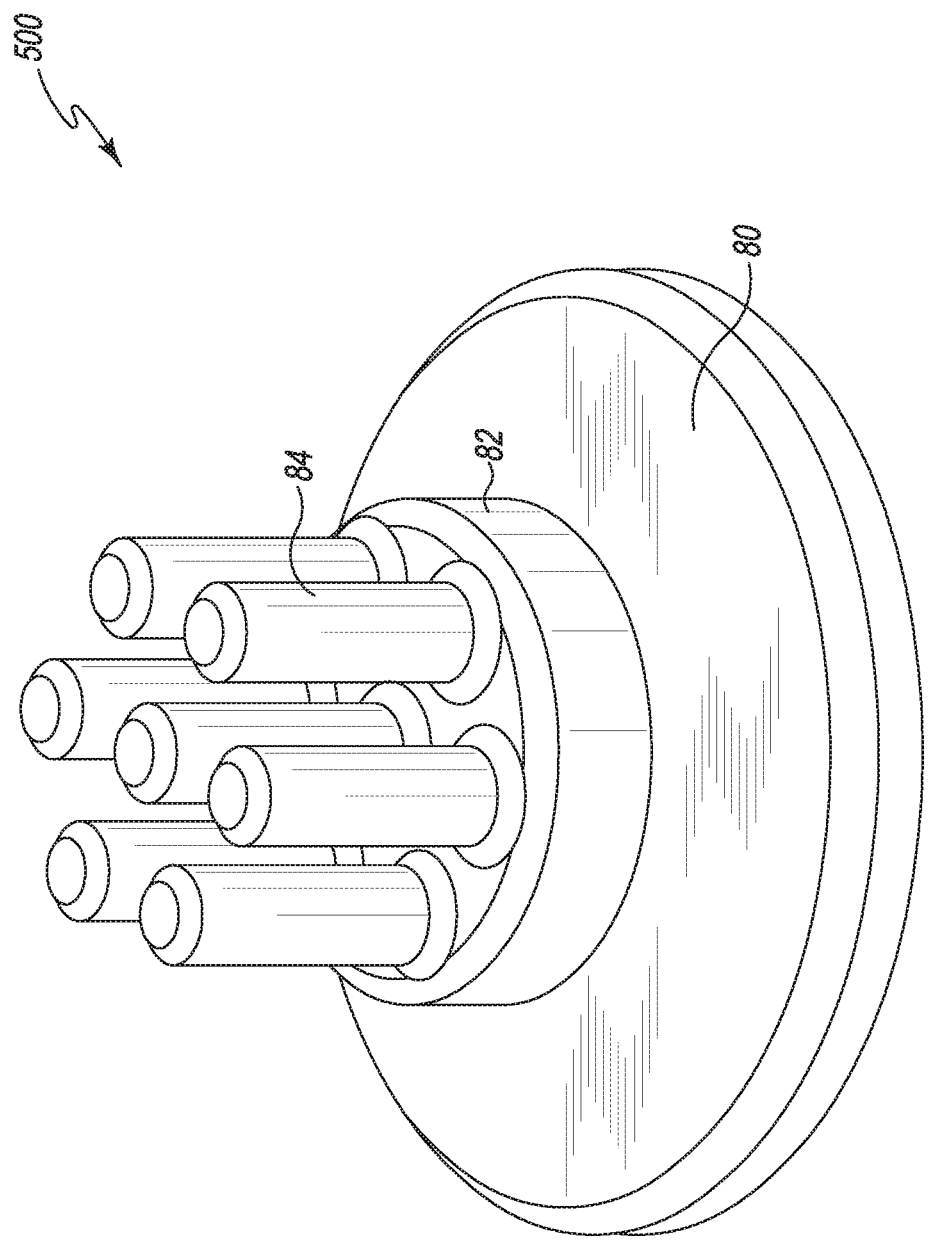
FIG. 14 is a perspective view of a small undercast.
Figure 15:
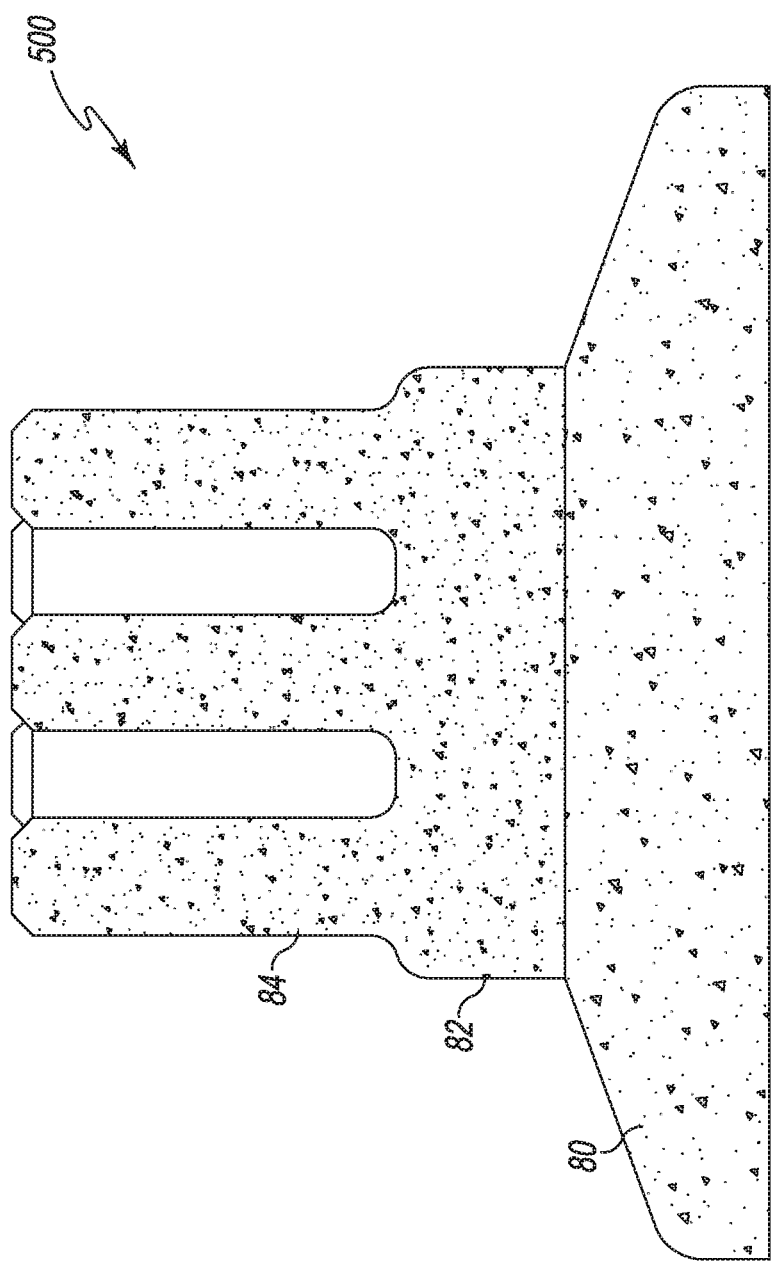
FIG. 15 is a cross-sectional view of the small undercast.

Referring to FIGS. 14 and 15, in some embodiments, the small undercast 500 comprises a base 80, an intermediate section 82, and at least one member 84 extending outwardly from the intermediate section 82. In some embodiments, the base is coupled to the intermediate section, and the intermediate section is coupled to the at least one member 84.

In some embodiments, the at least one member 84 is selected from a group consisting of a tine, a post, and a cone. The size, shape, pattern, and number of the at least one member 84 will depend on the desired number, size, and location of pores to be produced in the perfusible-tissue construct 102. A person of skill in the art will recognize that the small undercast 500 may be configured with any number of at least one members 84. In some embodiments, the small undercast 500 comprises at least one member, at least two members, at least three members, at least four members, at least five members, at least six members, at least seven members, at least eight members, at least nine members, at least ten members, at least fifteen members, at least twenty members, or at least 25 members.

In some embodiments, the at least one member 84 has a bottom circumference of about 10 micrometers to about 5,000 micrometers, and a top circumference of about 10 micrometers to about 5,000 micrometers. In some embodiments, the at least one member 84 has a bottom circumference of at least 10 micrometers, at least 20 micrometers, at least 30 micrometers, at least 40 micrometers, at least 50 micrometers, at least 60 micrometers, at least 70 micrometers, at least 80 micrometers, at least 90 micrometers, or at least 100 micrometers. In some embodiments, the at least one member 84 has a bottom circumference of about 100 micrometers, about 200 micrometers, about 300 micrometers, about 400 micrometers, about 500 micrometers, about 600 micrometers, about 700 micrometers, about 800 micrometers, about 900 micrometers, or about 1,000 micrometers. In some embodiments, the bottom circumference of the at least one member 84 ranges from about 500 micrometers to about 1,000 micrometers, about 1,000 micrometers to about 1,500 micrometers, about 1,500 micrometers to about 2,000 micrometers, about 2,000 micrometers to about 2,500 micrometers, about 2,500 micrometers, to about 3,000 micrometers, about 3,000 micrometers to about 3,500 micrometers, about 3,500 micrometers to about 4,000 micrometers, about 4,000 micrometers to about 4,500 micrometers, or about 4,500 micrometers to about 5,000 micrometers.

A person having skill in the art will recognize that the size (including height, width, or circumference) of the at least one member 84 will vary depending on the desired pore size in the perfusible tissue construct 102. In some embodiments, the at least one member 84 is round. In some embodiments, the at least one member 84 has the shape of a square, rectangle, polygon, star, triangle, or amorphous. In some embodiments the diameter of the at least one member 84 is about 0.01 cm to about 3 cm.

A person having skill in the art will recognize that the pattern of the at least one member 84 may be generated as desired by the person's having skill in the art preferred location for generated pores in the perfusible-tissue construct 102.

In some embodiments, the at least one member 84 of the small undercast 500 is configured to couple with at least one opening 46 of the platen 300, described further below. In some embodiments, the cell micro-tissues captured in the capture container 200 are placed in the porous section 42 of the platen 300. The cell microtissues assemble around the at least one member 84 and fuse to each other to generate a perfusible tissue construct 102 when the undercast is removed and the space left by the at least one member 72 forms a perfusible opening contiguous with the at least one opening 46 of the platen 300. In this embodiment, the shape, size, pattern, and number of the at least one member 84 will be limited by the shape, size, and number of the at least one opening 46 of the platen 300.

In some embodiments, the at least one member 84 is positioned to traverse the at least one opening 46 of the platen 300. In some embodiments, the at least one member 84 comprises a material to prevent cell adhesion. In some embodiments, the at least one member 84 is coated with a material to prevent cell adhesion. Examples of a material to prevent cell adhesion are silicone, polyHEMA, and agarose.

In some embodiments, the small undercast 500 is not limited to a single shape. In one embodiment, the small undercast 500 has an annular shape. Without being limited, the small undercast 500 may be shaped similar to a polygon, a square, a rectangle, a triangle, a star, or a circle.

The small undercast 500 is made of a biocompatible material that remains stable when autoclaved. In one embodiment, the small undercast 500 is made of a polymer that remains stable when autoclaved. In some embodiments, the small undercast 500 is made of a material that is optically clear. In one embodiment, the material is chosen from a group consisting of ceramic, glass, metal, polymer, and a combination thereof. In one embodiment, the polymer comprises resin. In one embodiment, the polymer comprises at least about 95% resin. In one embodiment, the small undercast 500 is made of a resin. In one embodiment, the small undercast 500 is made of a polymer except the at least one member 84 is made of a resin. In some embodiments, the small undercast 500 is made of a silicone except the at least one member 84 is made of A2 Resin. In some embodiments, the small undercast 500 is made of A2 Resin. In some embodiments, the small undercast 500 is made of Filtek Silorane. In some embodiments, the small undercast 500 is made of a combination of A2 Resin and Filtek Silorane.

In one embodiment, the small undercast 500 is configured to fit into the well of a standard six-well plate. Examples of a standard six-well plate is Catalog No. 140675 six-well plate from THERMOFISHER SCIENTIFIC or Manufacture No. 657185 six-well plate from THOMAS SCIENTIFIC, Inc.

In some embodiments, a perfusible-tissue formation component 600 comprises a platen 300 coupled to a small undercast 500. The at least one opening 46 of the platen 300 is positioned to receive the at least one member 84 of the small undercast 500. The at least one member 84 of the small undercast 500 is positioned to and configured to traverse the at least one opening 46 of the platen 300.

In some embodiments, a perfusible-tissue formation component 600 comprises (i) a small undercast 500, comprising: (a) a base 80; (b) an intermediate section 82; and (c) at least one member 84, wherein the intermediate section 82 couples the base 80 to the at least one member 84, and wherein the at least one member 84 extends outwardly from the intermediate section 82; and (ii) a platen 300 comprising (a) a top surface 38 having a conically shaped platen reservoir 40, wherein the platen reservoir 40 comprises a vertex locating a porous section 42 having a flat surface 44 and at least one opening 46, and (b) a bottom surface 52 defining a platen channel 56; wherein the at least one opening 46 is positioned receive the at least one member 84, and wherein the perfusible tissue-formation component 600 is made of a biocompatible material that remains stable when autoclaved.

In some embodiments, the perfusible-tissue formation component 600 comprises a platen 300 and an undercast 400, or the perfusible-tissue formation component 600 comprises a platen 300 and a small undercast 500. In some embodiments, the perfusible-tissue formation component 600 further comprises a capture container 200. In some embodiments, the capture container 200 comprises a capture foundation 24 having a top surface 26 and a bottom surface 28, wherein the top surface 26 defines a conically shaped capture reservoir 30 having a vertex, and the bottom surface 28 defines a capture channel 36, and wherein the capture container 200 is made of a biocompatible material that remains stable when autoclaved. In some embodiments, the conically shaped capture reservoir 30 comprises a capture section 34 located at the vertex of the capture container reservoir 30. In some embodiments, the top surface 26 is configured to contact the flat outer edge 48 of the platen 300.

In some embodiments, the perfusible-tissue formation component 600 may be cleaned by adding 70% ethanol for about 5 minutes and then the reservoirs (40 and 66) can be filled with 3% hydrogen peroxide solution with a platinum diode placed into the reservoir (40 or 66). The hydrogen peroxide and platinum diode are available together in contact lens cleaning kits from local grocers. The hydrogen peroxide-platinum diode can incubate for about 3-6 hours to remove cell debris from the platen 300 and undercast 400 or small undercast 500. Following cleaning, the components are rinsed with water, dried, and autoclaved for about 15 minute sterilization cycle at about 121 deg C. In some embodiments, the step of autoclaving further includes at least about a 5 minute dry cycle. After the components have cooled, they are ready for use.

In some embodiments, the perfusible-tissue formation component 600 further comprises a production container 100. The production container 100 comprising a floor 2, a wall 4 extending from the floor 2, wherein the floor 2 and wall 4 define a production reservoir 6, a formation section 18 defined in the floor 2, wherein the formation section 18 comprises at least one well 8, and a grip 10 extending outwardly from the formation section 18; wherein the production container 100 is made of a biocompatible material that remains stable when autoclaved. In some embodiments, the production container 100 further comprises a production container channel 20 defined in the bottom surface 22. In some embodiments, the production container 100 wall 4 comprises a top edge 12. In some embodiments, the top edge 12 of the wall 4 is configured to contact the top surface 38 of the platen 300. In some embodiments, the wall 4 of the production container 100 is configured to envelope the platen foundation 49.

In some embodiments, a biofabrication system comprises a micro-tissue production component, a perfusible tissue formation component 600, and a bioreactor 700. In some embodiments, the bioreactor 700 comprises a base 86 and a lid 87. The bioreactor is configured to receive the production container 100, the capture container 200, the platen 300, the undercast 400, the small undercast 500, the perfusible-tissue formation component 600, or a combination thereof.

In some embodiments, the base 86 comprises a well 88 having a floor 90 and a wall 92. An inlet port 94 is in fluid communication with the well 88. In some embodiments, the inlet port 94 is coupled to the wall 92 of the well 88. An outlet port 96 is in fluid communication with the well 88. In some embodiments, the outlet port 96 is coupled to the floor 90 of the well 88. In some embodiments, the floor 90 of the well 88 further comprises a raised grip 98. In some embodiments, the raised grip 98 is coupled to and extends outwardly from the floor 90 of the well 88. In some embodiments, the raised grip 98 is annular. In some embodiments, the raised grip 98 is configured to receive the platen channel 56, the capture container channel 36, or the production container channel 20. In some embodiments, the raised grip 98 is configured to receive the platen channel 56 to form a seal generating a contiguous flow of fluid through the inlet port 94 and outlet port 96 so that when the platen 300 is coupled to the well 88, a fluid flows from the inlet port 94 into the well 88 into the platen reservoir 40 then to contact the porous section 42 and out through the outlet port 96. In some embodiments, a tissue construct 102 is in contact with the porous section 42, and fluid flows from the inlet port 96 into the well 88 making contact with the tissue construct 102 and then down into the opening 46 and out through the outlet port 96.

In some embodiments, the well 88 is configured to receive a production container 100, a capture container 200, a platen 300, an undercast 400, a small undercast 500, or a perfusible-tissue formation component 600. In some embodiments, the well 88 is configured to hold a volume of fluid of up to about 20 mL$^3$. In some embodiments, the well 88 is comparable to the well size of a standard 6-well plate. Examples of standard six-well plates include Catalog No. 140675 six-well plate from THERMOFISHER SCIENTIFIC or Manufacture No. 657185 six-well plate from THOMAS SCIENTIFIC, Inc.

In some embodiments, the base 86 comprises at least one well 88. In some embodiments, the base 86 comprises at least two wells, at least three wells, at least four wells, at least five wells, at least six wells, at least seven wells, at least eight wells, at least nine wells, at least ten wells, at least eleven wells, or at least twelve wells.

In some embodiments, each well 88 of the base 86 includes an inlet port 94 in fluid communication with the well 88, and an outlet port 96 in fluid communication with the well 88. The inlet port 94 is configured to move fluid into the well 88 and the outlet port is configured to move fluid out of the well 88 when the bioreactor 700 is coupled to a pump and tubing. A person having skill in the art will recognize that the flow of the fluid can be adjusted based on the size of tubing and power of the pump employed. The bioreactor 700 is not limited to any type of fluid. Without being limited, some examples of fluid that may pumped through the bioreactor 700 include cell culture media, body fluids (including, but not limited to, blood, serum, saliva, urine, lymph fluid, plasma), saline, water, buffer, dyes, or a combination thereof.

The base 86 is made of biocompatible material that remains stable when autoclaved. In some embodiments, the base 86 is made of polymer. In some embodiments, the base 86 is made of a material that is optically clear. In some embodiments, the base 86 is made of material selected from the group consisting of ceramic, glass, metal, polymer, or a combination thereof. In some embodiments, the base 86 comprises A2 Resin. In some embodiments, the base 86 comprises 95% A2 Resin. In some embodiments, the base 86 is made of A2 Resin.

In some embodiments, the lid 87 is configured to cover the cover a portion of the base 86. In some embodiments, more than one lid 87 is used to cover the base 86. In some embodiments, a single lid 87 is used to cover the base 86. In some embodiments, the lid 87 is made of a material that is optically clear. In some embodiments, the lid 87 is made of a material that is opaque. In some embodiments, the lid 87 is made of material the remains stable when autoclaved. In some embodiments, the lid 87 comprises glass, metal, polymer, or a combination thereof. In some embodiments, the lid 87 comprises a polymer. In some embodiments, the lid 87 is made of Silorane.

Figure 18:
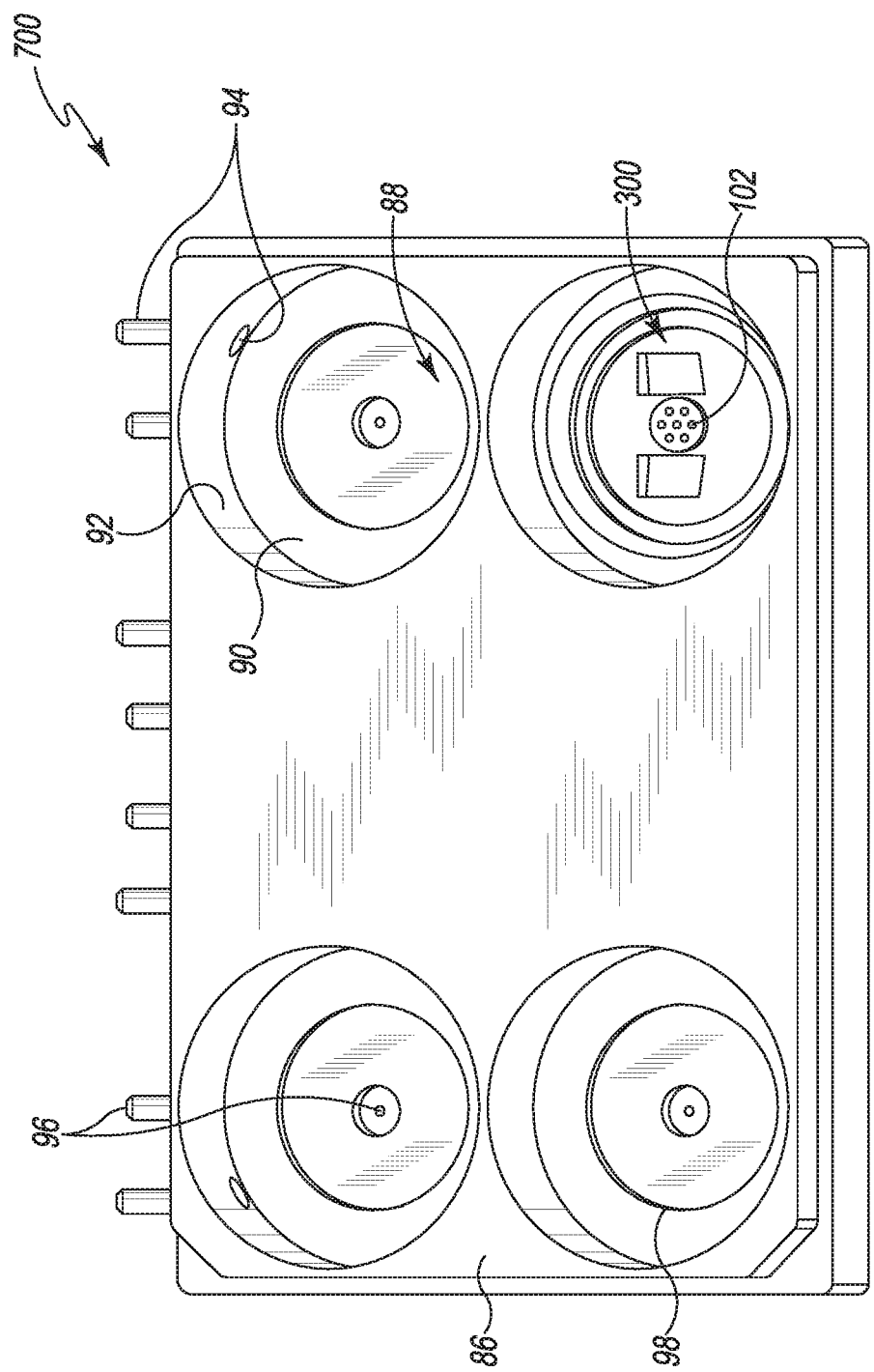
FIG. 18 is a top view of a bioreactor.
Figure 19:
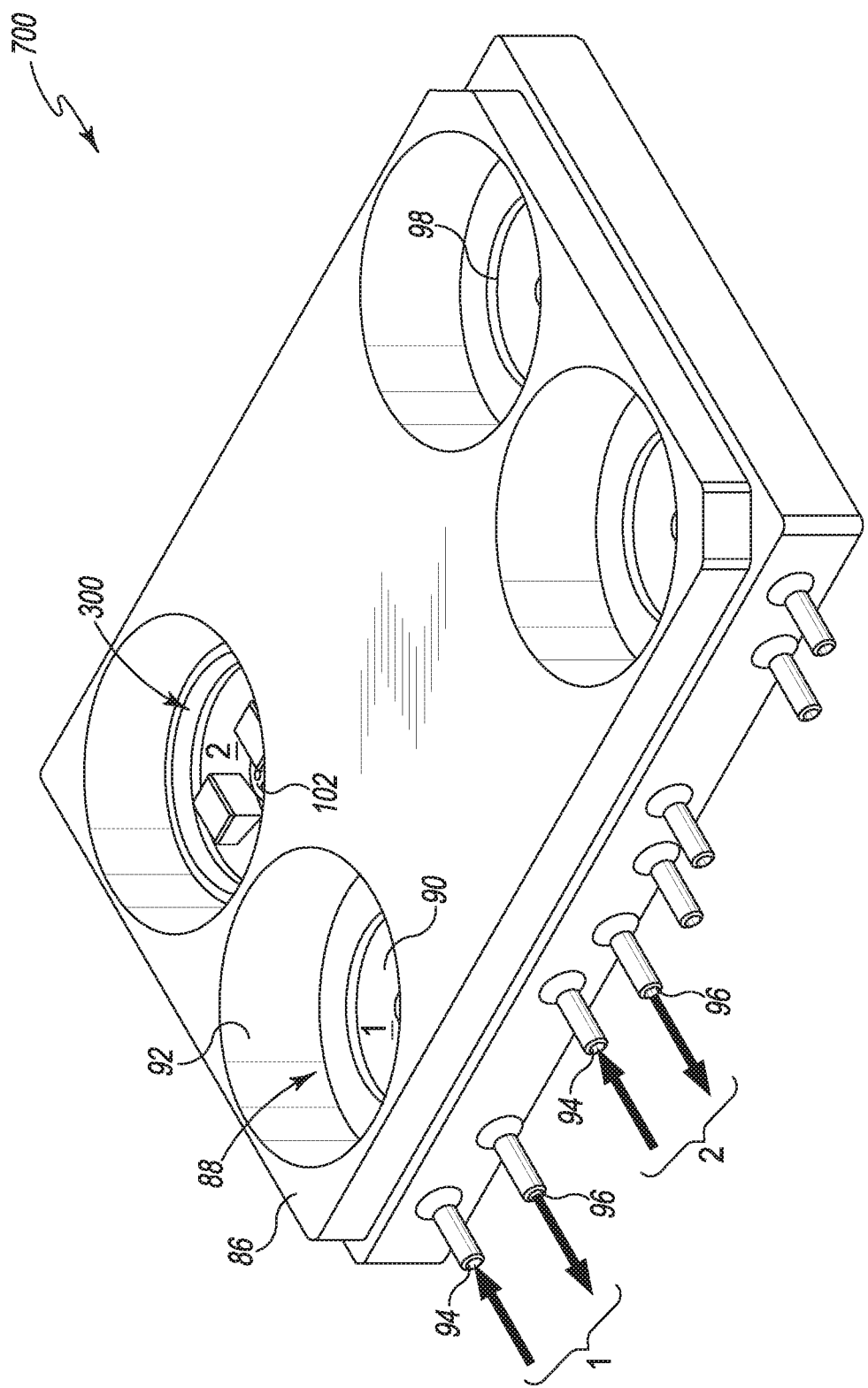
FIG. 19 is a perspective view of the bioreactor.

Referring now to FIGS. 18 and 19, in some embodiments, a bioreactor 700 comprises a base 86 and lid 87 (not shown), and further comprises a platen 300 comprising a perfusible-tissue construct 102. In some embodiments, the platen 300 comprises a top surface 38 having a conically shaped platen reservoir 40, wherein the platen reservoir comprises 40 a vertex locating a porous section 42 comprising a flat surface 44 and at least one opening 46, and a bottom surface 52 defining a platen channel 56; and wherein the platen 300 is made of a biocompatible material that remains stable when autoclaved. In some embodiments, the platen 300 is coupled to the base 86 of the bioreactor 700. In some embodiments, the well 88 of the base 86 is configured to receive the platen 300. In some embodiments, the platen channel 56 receives the raised grip 98. In some embodiments, a perfusible-tissue construct 102 is in contact with the porous section 42 of the platen 300. In some embodiments, the at least one opening 46 of the porous section 42 is positioned over the floor 90 over the outlet port 96 in fluid communication with the well 88 so that when fluid is pumped it travels from the inlet port 94 into the well 88, through the pores of the perfusible tissue construct 102, then through the at least one opening 46 and out of the well through the outlet port 96.

In some embodiments, the bioreactor 700 may be cleaned with ethanol to lyse attached cells followed by a PBS wash to remove cell debris. In some embodiments, the bioreactor 700 is autoclaved in a sealed container to protect sterility. In some embodiments, the bioreactor 700 is autoclaved for about 15 minutes on a sterilization cycle at about 121 deg C. In some embodiments, the step of autoclaving further includes a dry cycle for at least about 5 minutes. Once the components have cooled, they are ready to use.

In some embodiments, a kit is provided comprising a production container 100 in a packaging. In some embodiments, the kit further comprises a capture container 200. In some embodiments, a micro-tissue production component comprising a production container 100 and a capture container 200 in packaging. In some embodiments, a kit is provided comprising a platen 300 in packaging. In some embodiments, the kit further comprises an undercast 400 and or a small undercast 500. In some embodiments, a kit is provided comprising a perfusible-tissue formation component 600 comprising a platen 300 and an undercast 400 in packaging. In some embodiments, a kit comprising a perfusible-tissue formation component 600 comprising a platen 300 and a small undercast 500 in packaging. In some embodiments, a kit is provided comprising perfusible-tissue formation component 600 comprising a platen 300, an undercast 400, and a small undercast 500. In some embodiments, a kit is provided comprising a micro-tissue production component and a perfusible-tissue formation component 600. In some embodiments, a kit is provided comprising a bioreactor 700 comprising a base 86 and a lid 87. In some embodiments, a kit is provided comprising a bioreactor 700 and a micro-tissue production component. In some embodiments, a kit is provided comprising a bioreactor 700 and a perfusible-tissue formation component 600. In some embodiments, a kit is provided comprising a micro-tissue formation component, a bioreactor 700, and a perfusible-tissue formation component 600 in packaging.

In one embodiments, a kit is provided comprising (i) a micro-tissue production component having (a) a production container 100, comprising: a floor 2, a wall 4 extending from the floor 2, wherein the floor 2 and wall 4 define a production reservoir 6, and wherein the wall 4 includes a top edge 12, a formation section 18 defined in the floor 2, wherein the formation section 18 comprises at least one well 8, a grip 10 extending outwardly from the formation section 18, and (b) a capture container 200, comprising: a capture foundation 24 having a top surface 26 and a bottom surface 28, wherein the top surface 26 defines a conically shaped capture reservoir 30, and the bottom surface 28 defines a capture channel 36, wherein the top edge 12 of the production container 100 is positioned to contact the top surface 26 of the capture container 200, and wherein the micro-tissue production component is made of a biocompatible material that remains stable when autoclaved; and (ii) a perfusible-tissue formation component 600 comprising: (a) an undercast 400 comprising: a floor 58 having at least one relief port 60, a wall 62 extending outwardly from the floor 58, a perfusible-formation section 66 defined by a grip insert 68 surrounding a platform 70, and at least one member 72, wherein the at least one member 72 extends outwardly from the platform 70, wherein the perfusible-formation section 66 is coupled to the floor 58, and an undercast channel 64 defined by the floor 58, the wall 62, and the grip insert 68, wherein the undercast channel 64 extends between the wall 62 and the perfusible-formation section 66; and (b) a platen 300, comprising: a top surface 38 having a conically shaped platen reservoir 40, wherein the platen reservoir 40 comprises a vertex locating a porous section 42 comprising a flat surface 44 and at least one opening 46, and a bottom surface 52 defining a platen channel 56; wherein the platen channel 56 is positioned to receive the grip insert 68 of the undercast 400, and the at least one member 72 is configured to traverse the at least one opening 46 of the platen 300; and wherein the perfusible-tissue formation component 600 is made of a biocompatible material that remains stable when autoclaved; and (iii) a bioreactor 700, comprising: (a) a base 86 having at least one well 88 defined therein; wherein the at least one well 88 has a floor 90 and a wall 92, (b) at least one inlet port 94 in fluid communication with the at least one well 88, (c) at least one outlet port 96 in fluid communication with the at least one well 88, (c) a raised grip 98 coupled to and extending outwardly from the floor 90 of the well 88; and wherein the bioreactor 700 is made of a biocompatible material that remains stable when autoclaved. In some embodiments, the kit further comprises at least one lid 87 configured to cover at least a portion of the base 86.

In some embodiments, a method of forming a perfusible-tissue construct 102 is provided. The method comprises (i) culturing cells in a production container 100 to form at least one micro-tissue. In some embodiments, the production container 100 comprises a floor 2, a wall 4 extending from the floor 2, wherein the floor 2 and wall 4 define a production reservoir 6, and wherein the wall 4 includes a top edge 12, a formation section 18 defined in the floor 2, wherein the formation section 18 comprises at least one well 8, a grip 10 extending outwardly from the formation section 18, and wherein the production container 100 is made of biocompatible material that remains stable when autoclaved.

Next, the method comprises the step of removing the at least one micro-tissue from the production container 100 and placing it in a capture container 200, the capture container 200 comprising: a capture foundation 24 having a top surface 26 and a bottom surface 28, wherein the top surface 26 defines a conically shaped capture reservoir 30, and the bottom surface 28 defines a capture channel 36, and wherein the capture container 200 is made of a biocompatible material that remains stable when autoclaved.

Next the method comprises the step of centrifuging the capture container 200, and removing the centrifuged at least one micro-tissue from the capture container 200 and placing it onto a perfusible-tissue formation component 600 comprising an undercast 400 or small undercast 500 and a platen 300, and removing the undercast 400 or 500 from the platen 300 to reveal a perfusible-tissue construct 102.

In some embodiments, the method further comprises, placing the platen 300 comprising perfusible-tissue construct 102 into a bioreactor 700 comprising a base 86 having at least one well 88 defined therein; wherein the at least one well 88 has a floor 90 and a wall 92, at least one inlet port 94 in fluid communication with the at least one well 88, at least one outlet port 96 in fluid communication with the at least one well 88, a raised grip 98 coupled to and extending outwardly from the floor 90 of the well 88; and wherein the bioreactor 700 is made of a biocompatible material that remains stable when autoclaved, wherein the platen channel 56 is positioned to receive the raised grip 98 of the well 88, wherein the well 88 is configured to receive the platen 300.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A biofabrication system comprising
a production container including
a production floor having a top surface and a bottom surface,
a production wall extending from the top surface of the production floor, wherein the production floor and the production wall define a production reservoir,
a formation section defined in the top surface of the production floor, wherein the formation section comprises a formation well, wherein said formation well comprises a formation wall and a formation floor, optionally wherein the formation floor is concave, and
a grip extending outwardly from the formation floor through said formation section and into the production reservoir;
a capture container including
a capture foundation having a top surface and a bottom surface, wherein the top surface is configured to define a conically shaped capture reservoir having a vertex, and the bottom surface defines a capture channel;
wherein said capture foundation is configured to be positioned to contact the production container for transfer of material formed in the production container to the capture container;
a platen and an undercast, the platen and the undercast configured for receiving the material transferred to the capture container to form a tissue construct therein, the platen including a platen top surface and a platen bottom surface, wherein
(i) said platen top surface is configured to define a conically shaped platen reservoir having a vertex with a flat surface at a bottom of said platen reservoir, wherein said flat surface comprises at least one platen opening allowing fluid communication from the platen top surface and the platen bottom surface, and
(ii) said platen bottom surface is configured to define a platen channel;
the undercast configured to be coupled with the platen and including
an undercast floor comprising a relief port;
an undercast wall extending outwardly from a perimeter of said undercast floor;
an undercast grip extending from the undercast floor and concentric to said undercast wall to define a perfusible-formation section and an undercast member that extends outwardly from the perfusible-formation section and aligns with said at least one platen opening when said platen is coupled to said undercast; and
a bioreactor configured to receive the platen and the tissue construct therein, the bioreactor including:
(i) a bioreactor base having a bioreactor well defined therein; wherein the bioreactor well has a well floor and a well wall,
(ii) an inlet port in fluid communication with said bioreactor well, and
(iii) an outlet port in fluid communication with said bioreactor well,
wherein said production container, said capture container, said platen, said undercast, and said bioreactor are each made of a biocompatible material that remains stable when autoclaved.

2. The system of claim 1, further comprising a production container channel defined in the bottom surface of said production container.

3. The system of claim 1, wherein the vertex of the captured reservoir comprises a flat surface.

4. The system of claim 1, wherein the top surface of the production floor comprises a flat outer edge.

5. The system of claim 1, wherein the platen top surface further comprises a flat outer edge.

6. The system of claim 1, further comprising a grip extending outwardly from the platen top surface.

7. The system of claim 1, wherein the flat surface of the platen top surface includes a mesh screen affixed thereto.

8. The system of claim 1, wherein said undercast member is formed in a shape selected from a group consisting of a tine, a post, and a cone.

9. The system of claim 1, wherein said undercast member comprises a material to prevent cell adhesion.

10. The system of claim 1 further comprising a lid configured to cover at least a portion of the bioreactor, wherein the lid is composed of a biocompatible material that remains stable when autoclaved.

11. The system of claim 1, wherein the outlet port is in fluid communication with contents of the bioreactor well.

12. A perfusible-tissue formation component, comprising:
(i) an undercast comprising:
a floor having at least one relief port;
a wall extending outwardly from the floor;
an undercast channel defined by the wall;
a perfusible-formation section defined by a grip insert surrounding a platform, and at least one member, wherein the at least one member extends outwardly from the platform,
wherein the perfusible-formation section is coupled to the floor, and
wherein the undercast channel extends between the wall and the perfusible-formation section; and
(ii) a platen comprising:
a top surface having a conically shaped platen reservoir, wherein the platen reservoir comprises a vertex having a flat surface and at least one opening, and
a bottom surface defining a platen channel;
wherein the platen channel is positioned to receive the grip insert of the undercast, and the at least one member traverses the at least one opening; and
wherein the perfusible-tissue formation component is made of a biocompatible material that remains stable when autoclaved.

13. A method of forming a perfusible-tissue construct, said method comprising:
(i) culturing cells in a production container to form a micro-tissue, the production container comprising:
a production floor having a top surface and a bottom surface,
a production wall extending from the top surface of the production floor, wherein the production floor and the production wall define a production reservoir,
a formation section defined in the top surface of the production floor, wherein the formation section comprises a formation well, optionally wherein formation well comprises a formation wall and a formation floor, optionally wherein the formation floor is concave, and a grip extending outwardly from the formation floor through said formation section and into the production reservoir, wherein the production container is made of a biocompatible material that remains stable when autoclaved;

(ii) transferring the micro-tissue formed in said production container to a capture container, said capture container comprising:

a capture foundation having a top surface and a bottom surface, wherein the top surface defines a conically shaped capture reservoir having a vertex, and the bottom surface defines a capture channel, and wherein the capture container is made of a biocompatible material that remains stable when autoclaved;

(iii) centrifuging the capture container, (iv) removing the micro-tissue from the capture container after step (iii) and placing the micro-tissue onto a perfusible-tissue formation component, said perfusible-tissue formation component comprising a platen and an undercast, wherein said platen comprises
(i) a platen top surface having a conically shaped platen reservoir, wherein the platen reservoir comprises a vertex having a porous section comprising a flat surface and at least one platen opening, and
(ii) a bottom surface defining a platen channel; and said undercast comprises
an undercast floor comprising a relief port;
an undercast wall extending outwardly from a perimeter of said undercast floor;
an undercast grip extending from the undercast floor and concentric to said undercast wall to define a perfusible-formation section and an undercast member that extends outwardly from the perfusible-formation section and aligns with said at least one platen opening when said platen is coupled to said undercast;

wherein the bottom surface of the platen is configured to couple with said undercast, and wherein the perfusible tissue-formation component is made of a biocompatible material that remains stable when autoclaved; and (v) removing the undercast from the platen to obtain the formed perfusible-tissue construct.

14. The method of claim 13, further comprising placing the platen comprising the formed perfusible-tissue construct into a bioreactor comprising:

(a) a bioreactor base having a bioreactor well defined therein; wherein the bioreactor well has a well floor and a well wall, (b) an inlet port in fluid communication with said bioreactor well, (c) an outlet port in fluid communication with said bioreactor well, (d) a raised grip coupled to and extending outwardly from said well floor; and wherein the bioreactor is made of a biocompatible material that remains stable when autoclaved, wherein the platen channel is positioned to receive the raised grip of the bioreactor.

15. The method of claim 14, further comprising perfusing the formed perfusible-tissue construct by flowing a media through the bioreactor using tubing and a pump configured to control a flow of the media.

* * * * *